(12) United States Patent
Sakata et al.

(10) Patent No.: US 7,491,303 B2
(45) Date of Patent: Feb. 17, 2009

(54) MEASURING INSTRUMENT AND CONCENTRATION MEASURING DEVICE

(75) Inventors: Tetsuya Sakata, Kyoto (JP); Tokuo Kasai, Kyoto (JP); Taizo Kobayashi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 715 days.

(21) Appl. No.: 10/491,120

(22) PCT Filed: Sep. 27, 2002

(86) PCT No.: PCT/JP02/10137

§ 371 (c)(1),
(2), (4) Date: Mar. 26, 2004

(87) PCT Pub. No.: WO03/029804

PCT Pub. Date: Apr. 10, 2003

(65) Prior Publication Data

US 2004/0244151 A1 Dec. 9, 2004

(30) Foreign Application Priority Data

Sep. 28, 2001 (JP) ............................. 2001-301009
Mar. 20, 2002 (JP) ............................. 2002-078183

(51) Int. Cl.
*G01N 27/327* (2006.01)

(52) U.S. Cl. ............. 204/400; 204/403.01; 204/403.02; 204/416

(58) Field of Classification Search ...........................
204/403.01–403.05, 416–418, 400; 205/777.5, 205/775, 778, 792
See application file for complete search history.

(56) References Cited

U.S. PATENT DOCUMENTS

| 4,963,245 | A | * | 10/1990 | Weetall | 205/777.5 |
| 5,126,034 | A | * | 6/1992 | Carter et al. | 204/403.05 |
| 5,384,028 | A | | 1/1995 | Ito | 257/253 |
| 6,616,819 | B1 | * | 9/2003 | Liamos et al. | 204/403.02 |
| 6,827,829 | B2 | * | 12/2004 | Kawanaka et al. | 204/403.02 |
| 2003/0042150 | A1 | * | 3/2003 | Ryu et al. | 205/778 |

FOREIGN PATENT DOCUMENTS

EP 0 471 986 2/1992

(Continued)

OTHER PUBLICATIONS

JPO computer English language translation of Hiroshi JP 2000-019147 A , application published Jan. 21, 2000.*

(Continued)

*Primary Examiner*—Alex Noguerola
(74) *Attorney, Agent, or Firm*—Hamre, Schumann, Mueller & Larson, P.C.

(57) ABSTRACT

The measurement instrument includes an attribute information output section to output attribute information about the attributes of the measurement instrument as an electric physical value. The attribute information is based on at least one of the conditions including a resistance of the attribute information output section, a location of the attribute information output section, and the size of a region on which the attribute information output section is formed. The attribute information may be used to select the calibration curve suitable for the measurement instrument. The attribute information may be one that relates to a specific measurement standard applied to the measurement instrument.

16 Claims, 23 Drawing Sheets

FOREIGN PATENT DOCUMENTS

| | | |
|---|---|---|
| EP | 1 118 856 | 7/2001 |
| EP | 1 152 239 | 11/2001 |
| JP | 4-357452 | 12/1992 |
| JP | 7-209242 | 8/1995 |
| JP | 8-10208 | 1/1996 |
| JP | 8-20412 | 1/1996 |
| JP | 8-43405 | 2/1996 |
| JP | 8-94629 | 4/1996 |
| JP | 10-332626 | 12/1998 |
| JP | 2000-19147 | 1/2000 |
| JP | 2000-171427 | 6/2000 |
| JP | 2001-311711 | 11/2001 |

OTHER PUBLICATIONS

JPO computer English language translation of Hiroshi JP 10-332626 A, application published Dec. 18, 1998.*

JPO computer English language translation of Masaji et al. JP 2001-311711 A, application published Nov. 9, 2001.*

JPO computer English language translation of Yoshiyuki et al. JP 08-043405 A, application published Feb. 16, 1996.*

JPO computer English language translation of Akihiro et al. JP 08-094629 A, application published Apr. 12, 1996.*

\* cited by examiner

FIG.5

| Disconnection Pattern | Measurement Standard | Calibration Curve |
|---|---|---|
| 1 | 1 | 1 |
| 2 | 1 | 2 |
| 3 | 1 | 3 |
| 4 | 2 | 1 |
| 5 | 2 | 2 |
| 6 | 2 | 3 |
| 7 | 3 | 1 |
| 8 | 3 | 2 |
| 9 | 3 | 3 |

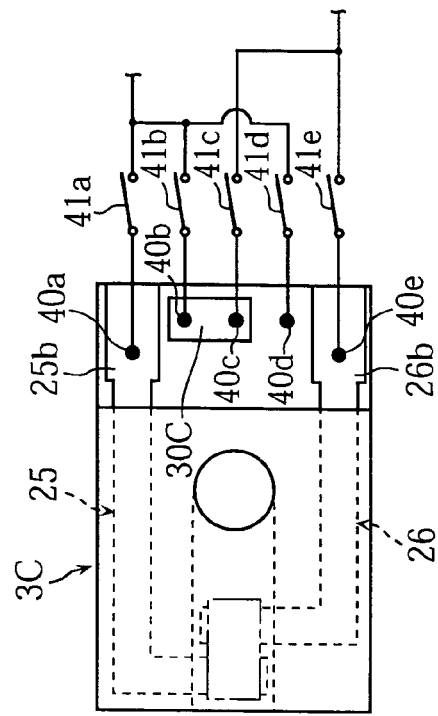
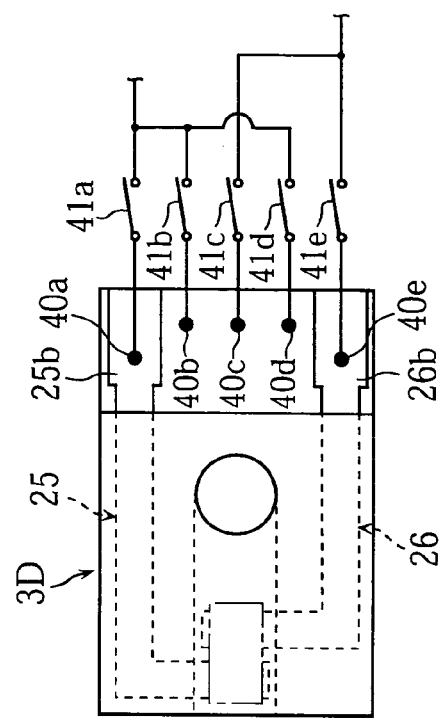
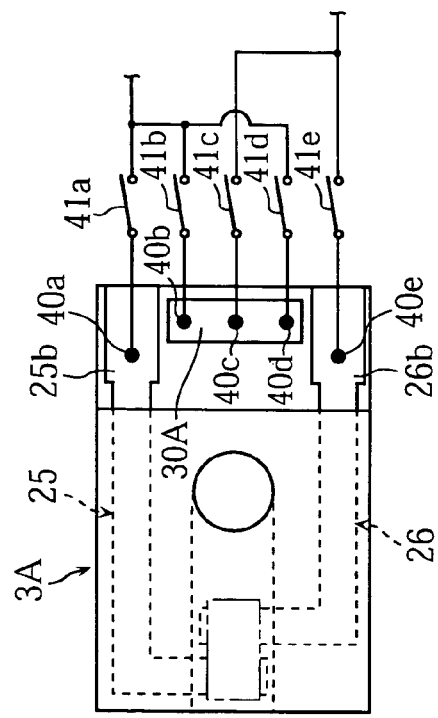
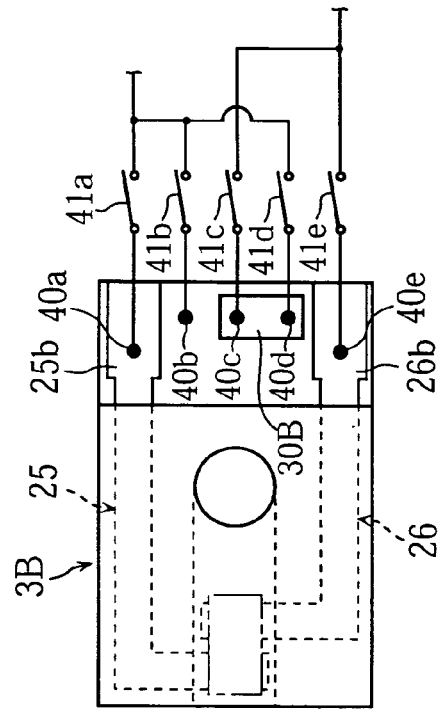

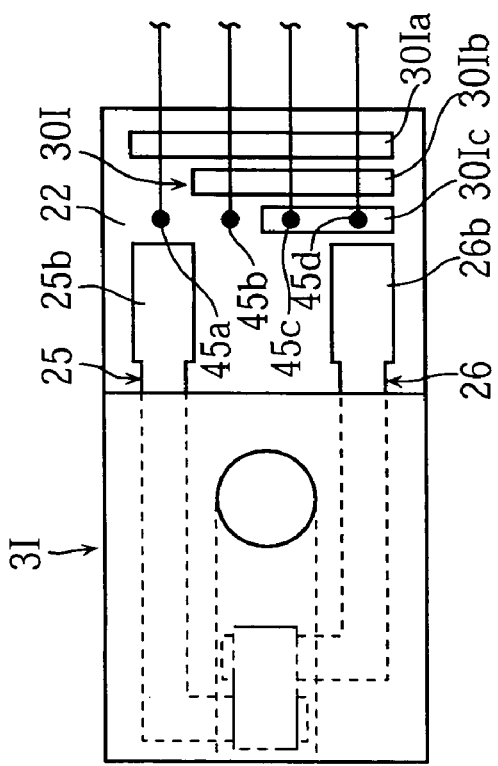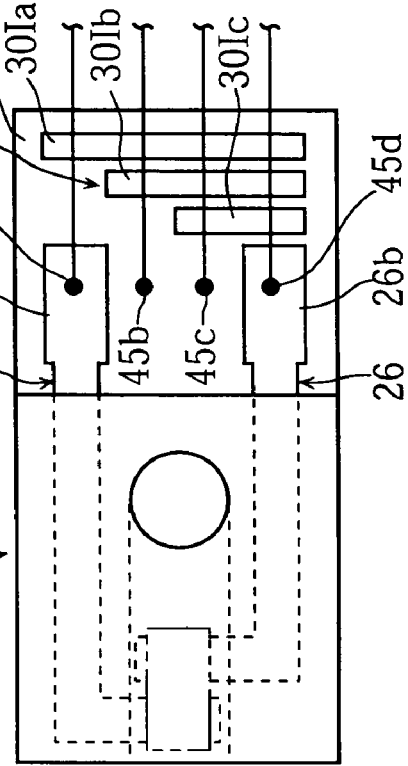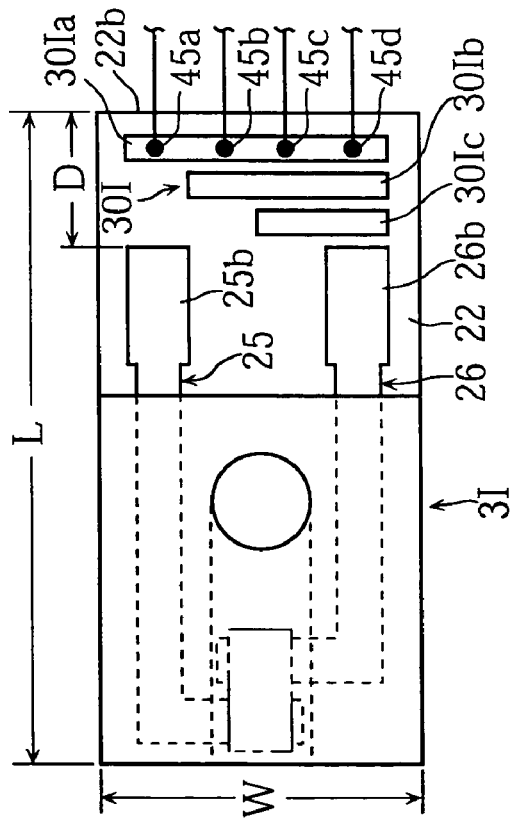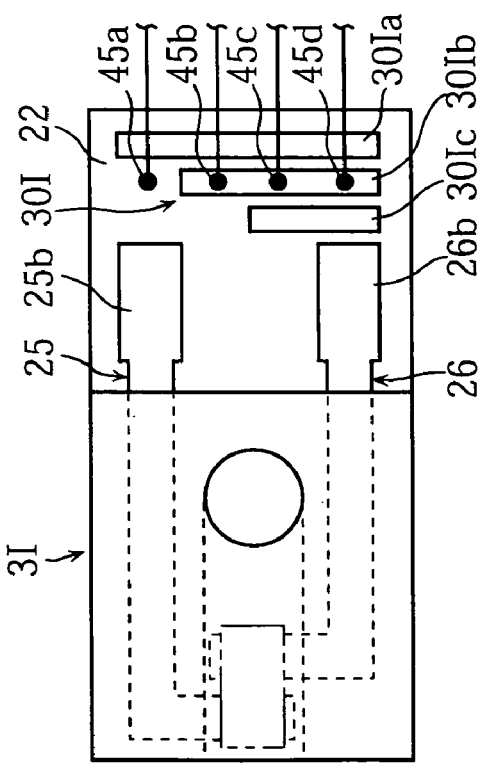

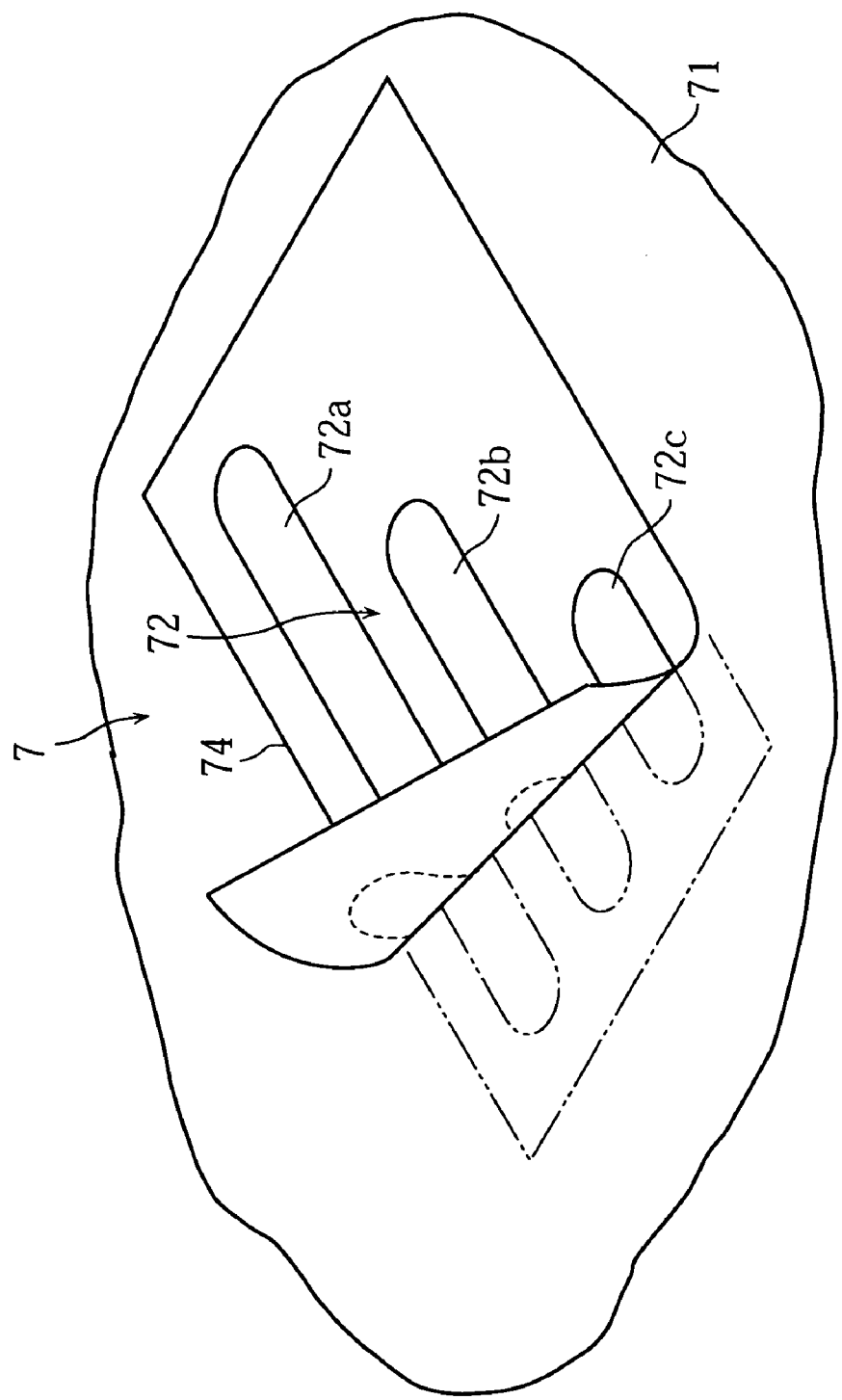

MEASURING INSTRUMENT AND CONCENTRATION MEASURING DEVICE

This application is a 371 of PCT/JP02/10137, filed on Sep. 27, 2002, which claims foreign priority from Japanese application 2001-301009, filed on Sep. 28, 2001, and Japanese application 2002-78183, filed on Mar. 20, 2002.

TECHNICAL FIELD

The present invention relates to a measurement instrument such as a biosensor, a method of making the measurement instrument, a set of the measurement instrument and a measurement auxiliary instrument, a sensor cartridge for accommodating a plurality of the measurement instruments, and a concentration measuring device for calculating the concentration of a specific component in a sample liquid with the measurement instrument.

BACKGROUND ART

In measuring a specific component in body fluid (e.g. glucose in blood), redox reaction is utilized in general. A handy-size blood measuring device is generally used for the easy measurement of blood sugar at or away from home. In use, a disposal biosensor for providing an enzyme reaction field is attached to this simple blood sugar measuring device. When supplied with blood, the biosensor measures blood sugar level in blood (see JP-B-H08-10208 for example).

The biosensors may be different in sensitivity. Such difference is often made by change in component materials or in design for production lines. Particularly on launching the production lines, optimization in production conditions and material selection may cause the biosensors to differ in sensitivity. Further, when the production of the biosensors is performed at a plurality of factories or one factory but on the plural production lines, the biosensors produced at the different factories or on the different lines may also differ in sensitivity. Therefore, the blood sugar measuring device is often provided in advance with a plurality of calibration curves to measure concentrations correctly with the biosensors varying in sensitivity. With the blood sugar measuring device capable of measuring a plurality of measurement items such as a blood sugar level and a cholesterol level, the plural calibration curves are needed for the measurement items. In these cases, the measuring device must recognize information about a calibration curve suitable for the sensitivity of the biosensor and the measurement items to select such a calibration curve.

As a first example method of determining the calibration curve, each calibration curve is assigned with an identification code in advance. The biosensor is also assigned with an identification code, which is displayed on a case of the biosensor or in a user instruction. In this example, the blood sugar measuring device is installed with a program for determining the calibration curve in advance. When a user operates a button in the blood sugar measuring device, the calibration curve is determined.

As a second example method for determining the calibration curve, the case accommodates the plural biosensors and a correction chip for outputting information about the calibration curve suited to the biosensor. In this example, when the correction chip is inserted into the blood sugar measuring device in the same manner as is the biosensor, the concentration measuring device determines the calibration curve automatically (see e.g. JP-A-H08-20412).

However, when the user determines the calibration curve by the button operation, the operation is a burden to the user. Further, he or she may forget to perform the operation. Similarly, the use of the correction chip is a burden to the user, and he or she may forget to determine the calibration curve. If the user forgets the determination of the calibration curve, the measurement of blood sugar level cannot be performed appropriately. This is because the determination of the calibration curve should not be entrusted to the user.

Particularly, the correction chip increases the production cost since it requires additional production lines besides the production lines for the biosensor.

The biosensor utilizes various enzymes. In measuring the blood sugar level of the same sample blood, using different enzymes produces different calculation results of the blood sugar level. There are a plurality of standards for measuring the blood sugar level in the world. Each standard provides the kind of enzyme and the required component of blood. For example, the enzyme may be hexokinase or glucose oxidase, while the sample blood may be whole blood or plasma.

Therefore, in countries where the measurement standard provides that hexokinase be used as an enzyme, the blood sugar level measured with glucose oxidase is not appropriate for determining whether or not a patient develops diabetes. Further, when the blood sugar measuring device calculates the blood sugar level with the biosensor utilizing hexokinase, the blood sugar level is not correctly calculated with the biosensor utilizing glucose oxidase.

SUMMARY OF THE INVENTION

It is therefore an object of the present invention to provide a concentration measurement utilizing a concentration measuring device and a measurement instrument, having an advantage in production cost, reducing a burden of user, and capable of performing more exact concentration measurement. First, when the concentration measurement is performed with the concentration measuring device having a plurality of selectable calibration curves, the concentration measuring device is made to be capable of selecting a calibration curve suitable for the measuring instrument. Second, the present invention prevents incorrect concentration measurement due to the difference between the measurement standard of the measurement instrument and that of the concentration measuring device.

According to a first aspect of the present invention, there is provided a measurement instrument used as an attachment to a concentration measuring device for calculating a concentration based on concentration measurement information, and outputting the concentration measurement information to the concentration measuring device. An attribute information output section is formed to output information about attributes of the measurement instrument as electric physical values. The attribute information is based on at least one of the conditions including a resistance of the attribute information output section, a location of the attribute information output section, and the size of a region on which the attribute information output section is formed.

The attribute information is utilized for enabling the concentration measuring device to select a calibration curve suitable for the measurement instrument. More specifically, the attribute information is used to select a calibration curve suitable for the sensitivity of the measurement instrument or to select a calibration curve suitable for preset measurement items in the measurement instrument. The attribute information may be about a measurement standard applied to the measurement instrument.

The attribute information may include the production data of the measurement instrument, the validity data, the manufacturer, the production site (e.g. the country of manufacture and the factory location), the identification number of the lot that includes the measurement instrument (the lot number).

The measurement standard is determined by the kind of enzyme and the sample state (e.g., whole blood or plasma) in the measuring instrument, whereas the standard is determined by the method of calculation in the concentration measuring device.

The attribute information output section may include a plurality of individual information output sections for outputting specific information as electric physical values.

The electric physical value is electric current, resistance, voltage, etc. The attribute information or individual information is identified by the amount of the electric physical value, the existence of the electric physical value (open-short signal) or the combination of them. More specifically, when the attribute information is provided based on the resistance of the attribute information output section, the content of the attribute information is represented by the magnitude of the electric physical value, for example. When the attribute information is provided based on the location of the attribute information output section, it is outputted by at least one of the open-short signal and the amount of the electric physical value for example. When the attribute information is provided based an amount of space formed with the attribute information output section, it is outputted by at least one of the open-short signal and the amount of the electric physical value for example.

When the attribute information is provided based on the resistance, the resistance is adjusted by varying length, thickness or width, or by selecting material for the attribute information output section.

The measurement instrument of the present invention further comprises a substrate at least including an end portion inserted into the concentration measuring device for the concentration measurement. The attribute information output section is a strip formed in the end portion and having a width of 2 mm and below.

The measurement instrument further comprises a substrate having an end portion inserted into the concentration measuring device for concentration measurement for example, and a calculation information output section formed on the end portion to output information for concentration calculation. The attribute information output section is formed between the calculation information output section and an inserting edge of the end portion of the substrate into the concentration measuring device.

The attribute information output section includes first and second portions to contact terminals of the concentration measuring device and one or a plurality of connection-breakable parts connecting the first and second portions. The attribute information output section is provided with the attribute information by selectively breaking or leaving intact at least one of the connection-breakable parts.

Preferably, when the measurement instrument is supplied with the attribute information based on a resistance of the attribute information output section, the measurement instrument of the present invention comprises a correction information output section for outputting correction information relating to the discrepancy between the actual resistance in the attribute information output section and a resistance preset in the attribute information output section.

Preferably, the attribute information output section outputs identification information for informing the concentration measuring device that the measurement instrument can output the information for concentration calculation.

According to a second aspect of the present invention, there is provided a method of making the measurement instrument including a step of forming an attribute information output section for outputting attribute information about attributes of a measurement instrument. The step comprises a first operation for forming first and second portions contacting terminals of the concentration measuring device and one or plurality of connection-breakable parts connecting the first and second portions, and a second operation for disconnecting one or plurality of connection-breakable parts selected from the connection-breakable parts.

The first step may be performed by applying a conductive material or a resistance material by screen printing.

The second step may be performed by drill machining, laser processing or etching.

According to a third aspect of the present invention, there is provided a measurement instrument used as an attachment to a concentration measuring device for calculating a concentration based on concentration measurement information, and outputting the concentration measurement information to the concentration measuring device. The measurement instrument includes a measurement standard information output section to output information about a measurement standard applied to the measurement instrument.

According to a fourth aspect of the present invention, there is provided a set comprising a measurement instrument and a measurement auxiliary instrument. The measurement instrument is used as an attachment to a concentration measuring device and outputting the concentration calculation information to the concentration measuring device. The measurement auxiliary instrument is used as an attachment to a concentration measuring device and formed with a measurement standard information output section for outputting the measurement standard information about a measurement standard applied to the measurement instrument.

"The measurement auxiliary instrument" is added to each lot including a plurality of measurement instruments and is used as an attachment to the concentration measuring device for enabling the concentration measuring device to recognize the characteristics of the measurement instruments.

According to the third and fourth aspects of the present invention, the measurement standard information is supplied in the same way as in the first aspect of the present invention utilizing the attribute information output section. The attribute information is provided based on at least one of a resistance of the attribute information output section, a location of the attribute information output section, and an amount of space formed with the attribute information output section. Of course, the measurement standard may be supplied in a different way from the first aspect of the present invention.

According to a fifth embodiment of the present invention, there is provided a concentration measuring device used with a measurement instrument. The measurement instrument has an attribute information output section for outputting attribute information about attributes of the measurement instrument. The attribute information is based on at least one of a resistance of the attribute information output section, a location of the attribute information output section, and the size of a region on which the attribute information output section is formed. The concentration measuring device comprises a recognizer for recognizing or detecting the attribute information, and performs a specific operation relating to a concentration measurement based on the attribute information recognized by the recognizer.

The measurement instrument includes the attribute information output section for outputting the attribute information as calibration curve determination information for selecting a calibration curve suitable for the measurement instrument. The concentration measuring device comprises a storage unit for storing information about a plurality of calibration curves, a calibration curve selection unit selecting a specific calibration curve suitable for the measurement instrument from the calibration curves based on the attribute information for example.

The determination of the calibration curve may depend on the sensitivity or the preset measurement items (e.g. for glucose measurement or cholesterol measurement) of the measurement instrument.

The attribute information output section may output the attribute information as measurement standard information about a measurement standard applied to the measurement instrument. The concentration measuring device comprises a judging unit determining whether or not to perform concentration measurement with the measurement instrument based on the attribute information.

The attribute information output section may be output the attribute information including the production date, the validity date, the manufacturer, the production site (e.g. country of manufacture and factory location), an identification number of the lot including the measurement instrument (lot number).

The recognition means has a plurality of terminals contacting the attribute information output section, recognizing the attribute information in applying a constant voltage or current to the attribute information output section via the terminals.

According to a sixth embodiment of the present invention, there is provided a sensor cartridge having a plurality of measurement instruments for outputting concentration measurement information relating to a concentration of a specific component in a sample liquid, the cartridge being used as an attachment to a concentration measuring device for calculating the concentration of the specific component based on concentration measurement information. The sensor cartridge comprises an attribute information output section for outputting attribute information about attributes of the measurement instruments.

Typically, the attribute information is based on at least one of conditions including a resistance of the attribute information output section, a location of the attribute information output section, and the size of a region on which the attribute information output section is formed. Other structures may be used to output the attribute information.

The attribute information is used to select a calibration curve suitable for the measurement instruments depending on the sensitivity or the preset measurement items of the measurement instruments. The attribute information may include a measurement standard applied to the measurement instruments, the production date, the validity date, the manufacturer, the production site (e.g. country of manufacture and factory location), an identification number of the lot including the measurement instruments (lot number).

According to a seventh aspect of the present invention, there is provided a concentration measuring device with a sensor cartridge accommodating a plurality of measurement instruments, performing concentration calculation based on concentration measurement information from the measurement instrument taken out of the sensor cartridge having an attribute information output section for outputting attribute information about attributes of the measurement instruments. The concentration measuring device comprises a recognizer for recognizing the attribute information, and performs a specific operation relating to a concentration measurement based on the attribute information recognized by the recognition means.

The attribute information of the measurement instrument is based on at least one of the conditions including a resistance of the attribute information output section, a location of the attribute information output section, and the size of a region on which the attribute information output section is formed.

Preferably, when the attribute information is used to select a calibration curve suitable for the measurement instruments, the concentration measuring device comprises a storage unit storing information about a plurality of calibration curves, and a calibration curve selection unit selecting a specific calibration curve suitable for the measurement instrument from the calibration curves.

The concentration measuring comprises a cartridge mount for mounting the sensor cartridge and a plurality of terminals for contacting the attribute information output section. Preferably, the terminals contact the attribute information output section when the sensor cartridge is being mounted or after the cartridge has been mounted.

BRIEF DESCRIPTION OF THE DRAWINGS

FIG. 5 is a correspondence table of a disconnection pattern, a measurement standard and a calibration curve;

FIGS. 10A-10D are plan views illustrating a second embodiment of the present invention;

FIGS. 18A-18D are plan views showing a seventh embodiment of the present invention;

FIG. 27 is a perspective view showing a principal portion of the sensor cartridge.

BEST MODE FOR CARRYING OUT THE INVENTION

Preferred embodiments of the present invention will be described below with reference to the accompanying drawings.

FIGS. 1-9 show a first embodiment of the present invention.

Figure 1:
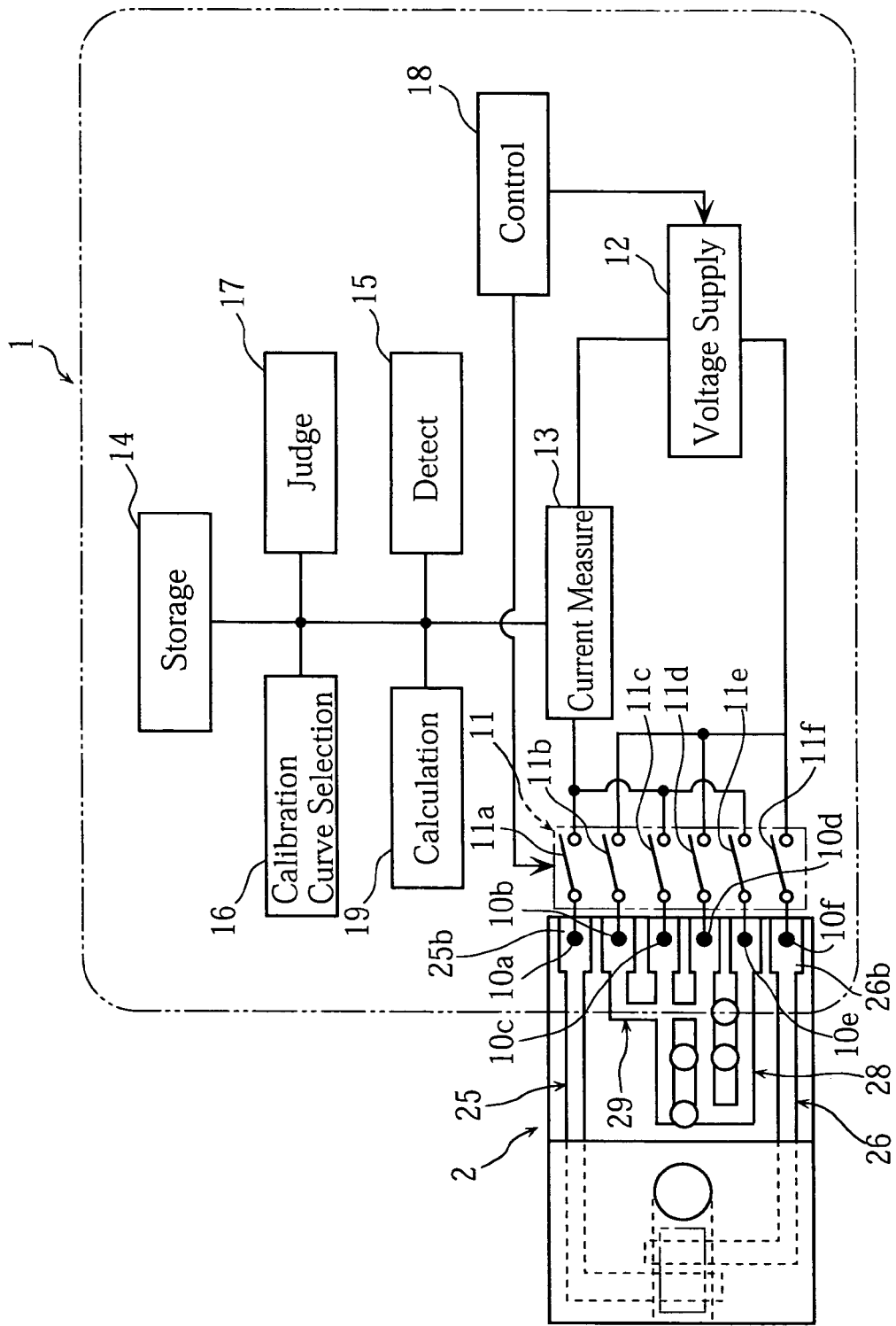
FIG. 1 is a schematic view showing a concentration measuring device with a biosensor according to a first embodiment of the present invention.

As shown in FIG. 1, a concentration measuring device 1 with a biosensor 2 mounted thereto is used for calculating the concentration of a specific component in a sample liquid. The concentration measuring device 1 includes first-sixth terminals 10a-10f, a switch unit 11, a voltage applying unit 12, an electric current measuring unit 13, a storage unit 14, a detection unit 15, a calibration curve selection unit 16, a judging unit 17, a control unit 18 and a calculating unit 19.

Figure 2:
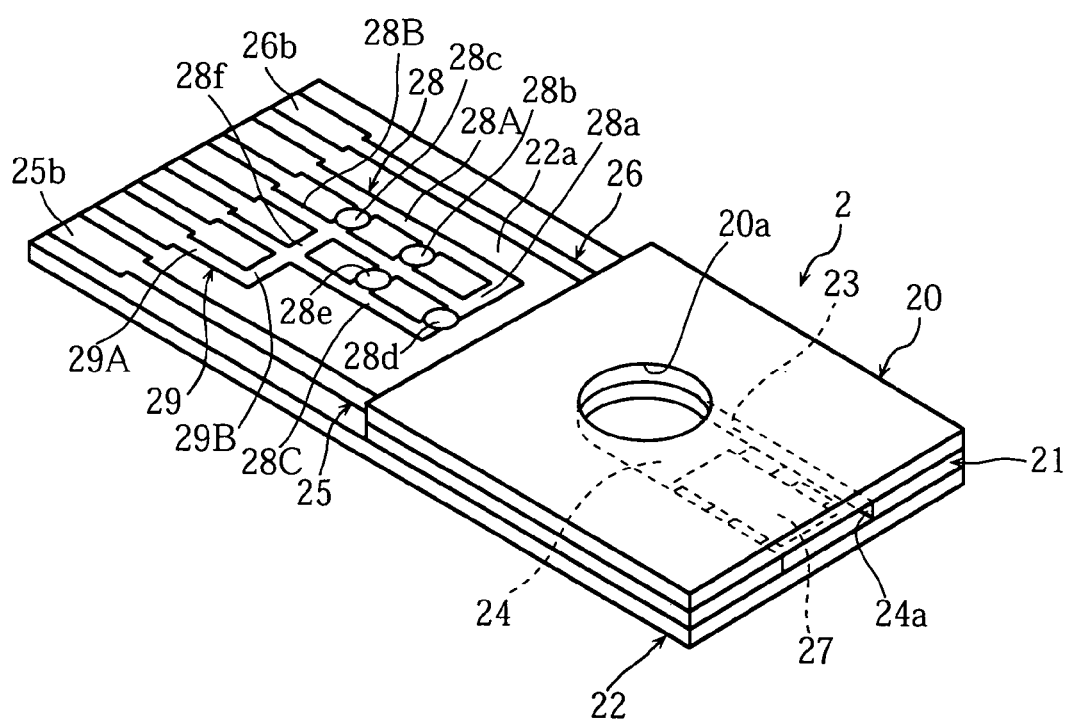
FIG. 2 is a perspective view of the biosensor shown in FIG. 1.
Figure 3:
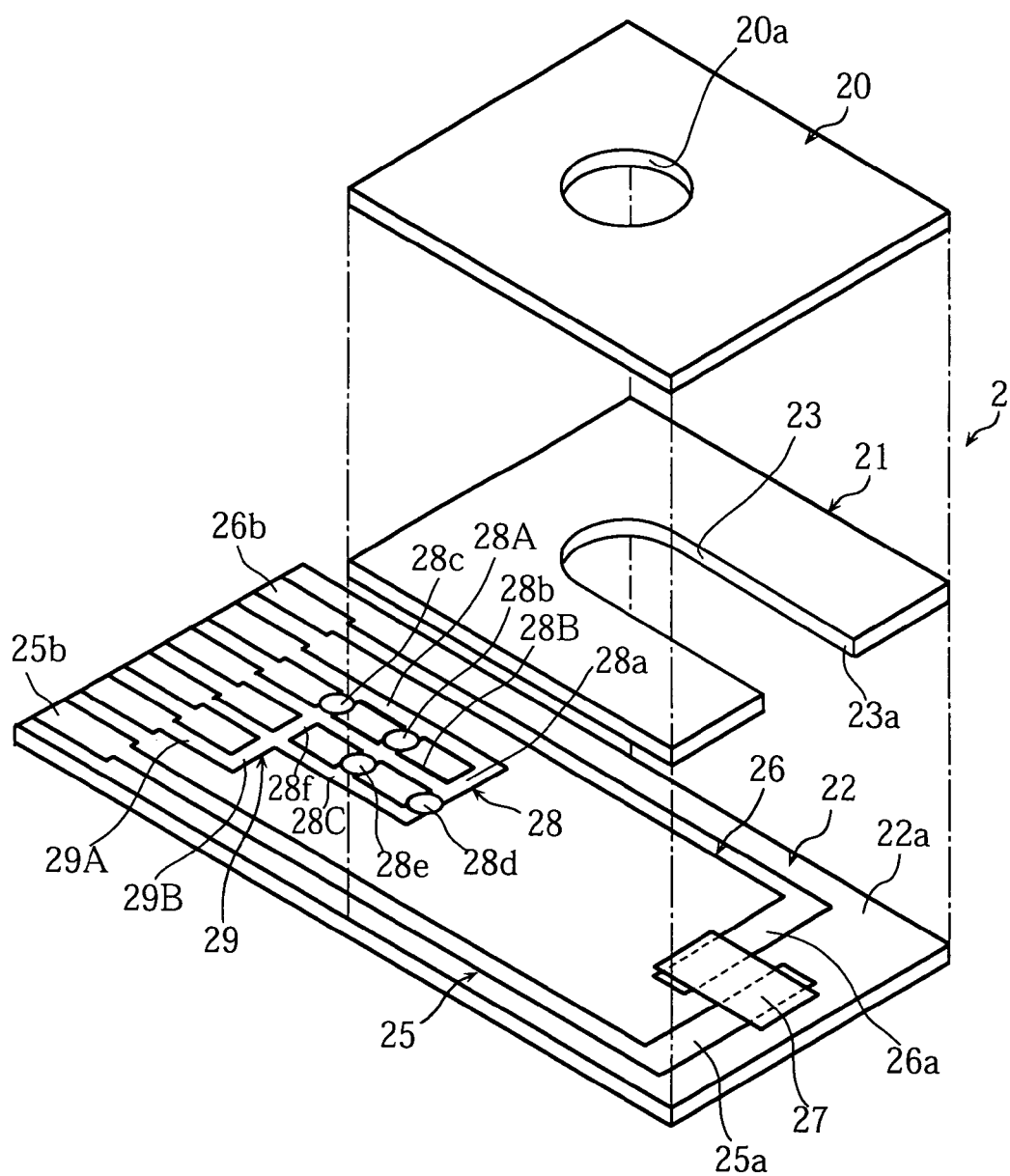
FIG. 3 is an exploded perspective view of the biosensor shown in FIG. 2.
Figure 4G:
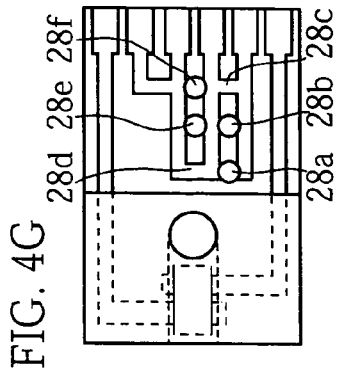
FIGS. 4A-4I are plan views illustrating examples of disconnection patterns.
Figure 4H:
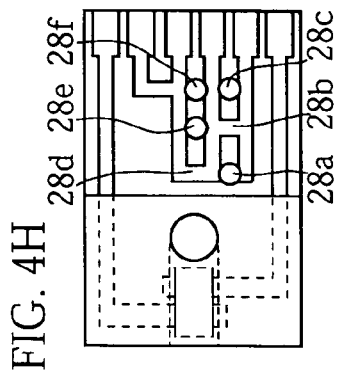
Figure 4I:
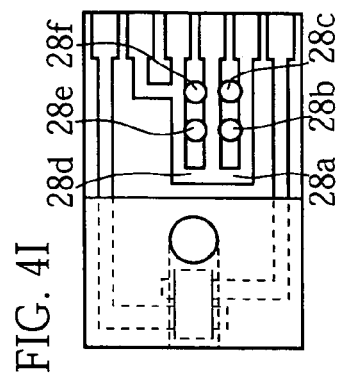
Figure 4D:
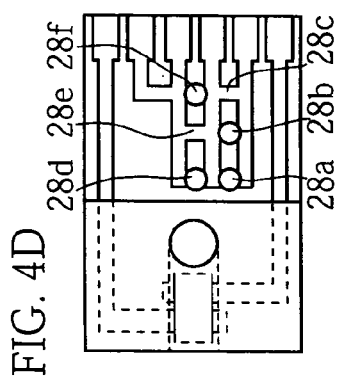
Figure 4E:
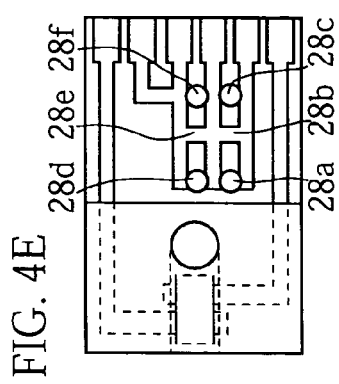
Figure 4F:
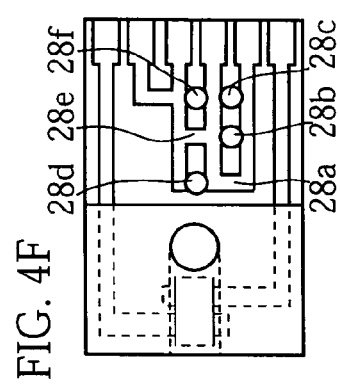
Figure 4A:
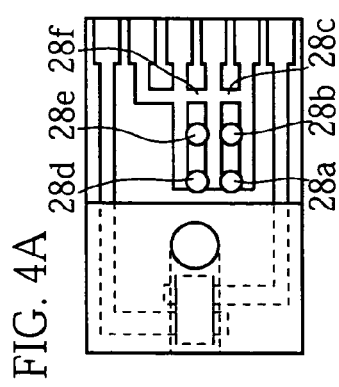
Figure 4B:
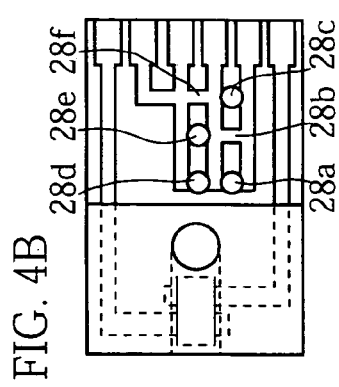
Figure 4C:
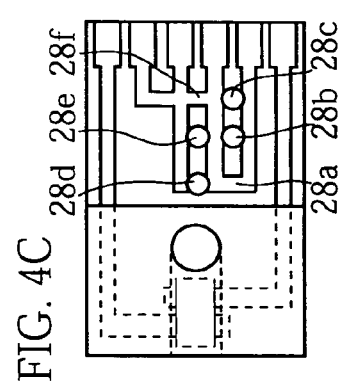

As shown in FIGS. 2 and 3, the biosensor 2 includes a cover 20, a spacer 21 and a substrate 22, these members forming a channel 24.

The channel 24 communicates with outside via a hole 20a formed in the cover 20 and an opening 23a of a slit 23 formed in the spacer 21. The opening 23a serves as a sample liquid inlet 24a. The sample liquid fed via the inlet 24a flows through the channel 24 toward the hole 20a by capillary action.

The substrate 22, made of resin such as PET, is rectangular. The substrate 22 has a length of 10-50 mm, a width of 5-20 mm, a thickness 0.5-2 mm for example. The substrate 22 has an upper surface 22a formed with a working electrode 25, a counterpart electrode 26, a reagent part 27, an attribute information output section 28 and a correction information output section 29.

The working electrode 25 and the counterpart electrode 26 mostly extend longitudinally of the substrate 22, while having ends 25a, 26a extending widthwise of the substrate 22. Thus, the working electrode 25 and the counterpart electrode 26 are L-shaped as a whole. The working and counterpart electrodes 25, 26 have ends 25b, 26b serving as terminals for contacting the first and sixth terminals 10a and 10f of the measuring device 1 (see FIG. 1). The working and counterpart electrodes 25, 26 may be formed by screen printing. Specifically, a mask, formed with openings corresponding the working and counterpart electrodes 25, 26, is put on the substrate 22 (normally, on a material substrate in which a plurality of regions for the substrates 22 are set). Then, material ink is supplied to fill the openings and dried. The material ink may be made by dissolving conductive powder and binder resin in a solvent. The working and counterpart electrodes 25, 26 have a thickness 10-20 μm, for example.

The reagent part 27 may be a solid element bridging between the end 25a of the working electrode 25 and the end 26a of the counterpart electrode 26. The reagent part 27 may contain a relatively large amount of mediators (electron carriers) into which a relatively small amount of redox enzymes are dispersed.

The electron carrier may be a Fe or Ru complex. The Fe complex may be potassium ferricyanide. The Ru complex may have a $NH_3$ ligand.

The determination of the redox enzyme depends on the type of the specific component to be measured. The specific component may be glucose, cholesterol or lactic acid. For such specific components, the redox enzyme may be glucose dehydrogenase, glucose oxidase, cholesterol dehydrogenase, cholesterol oxidase, lactic acid dehydrogenase or lactic acid oxidase.

The attribute information output section 28 is used for outputting the attribute information of the biosensor 2. The output section 28 can output, to the concentration measuring device 1, information such as "calibration curve selection information" to select a calibration curve suitable for the sensitivity of the biosensor 2 and "measurement standard information" regarding the measurement standard adopted for the biosensor 2. Specifically, the output section 28 includes first-third leads 28A-28C, and the attribute information is outputted as an electric current (a resistance) when a voltage is applied across the first and second leads 28A, 28B or across the second and third leads 28B, 28C. Between the adjacent leads 28A-28C, six connection-breakable parts 28a-28f are provided. In the present embodiment, two connection-breakable parts are disconnected among the three connection-breakable parts between the adjacent leads. In this case, it is possible to provide nine disconnection patterns, as shown in FIGS. 4A-4I, and therefore to output nine types of information separately by selecting one of the disconnection patterns. Referring to FIG. 5, when three types of measurement standards and three types of calibration curves are set, with the combinations of them being corresponded to the respective disconnection patterns, the biosensor 2 can output information for identifying them. More specifically, the three disconnection patterns between the first and second leads 28A and 28B may correspond to the three predetermined types of measurement standards, while the three disconnection patterns between the second and third leads 28B and 28C may correspond to the three predetermined types of calibration curves. As a result, the three types of the measurement standards and calibration curves can be separately outputted.

Of course, the number of the leads and the connection-breakable parts are not limited to the illustrated embodiment, but may be otherwise. Further, the number of connection-breakable parts to be disconnected is not limited to the illustrated embodiment. In the case where three connection-breakable parts are set between the adjacent leads, the number of parts to be disconnected may be selected from 0-3. This arrangement allows the desired information to be selected from more pieces of information than where two connection-breakable parts are fixedly disconnected.

Referring to FIGS. 2 and 3, the correction information output section 29 corrects the output from the first through third leads 28A-28C. The section 29 includes a fourth lead 29A and a joint 29B between the fourth lead 29A and the third lead 28C. When a voltage is applied across the third lead 28C and the fourth lead 29A, correction information is outputted as a current (a resistance). Preferably, the concentration measuring device 1 may store the resistance preset for the fourth lead 29A. Based on the correction information, it is possible to recognize how much the actually measured resistance of the fourth lead 29A varies from the preset resistance for the fourth lead 29A. Thus, the concentration measuring device 1 can correct the output from the first through third leads 28A-28C based on the deviation of the actual resistance from the preset value.

The attribute information output section 28 and the correction information output section 29 can be formed by screen printing for example. The connection-breakable parts 28a-28f are formed to electrically connect the adjacent leads 28A-28C. Thereafter, each of the connection-breakable parts 28a-28f may be disconnected or not in accordance with a disconnection pattern which is determined based on the measurement standard for the biosensor 2 and the calibration curve (sensitivity of the biosensor 2) used for the concentration calculation. The disconnection of the connection-breakable parts 28a-28i is performed by e.g. machining with the use of a drill, laser processing or etching. The sensitivity of the biosensor 2 may be found by taking an actual measurement of the sensitivity of a given number of biosensors 2 selected from the group of biosensors produced under the same conditions. This is an effective method when the sensitivity of the biosensor 2 is unpredictable due to the possibility of changing in design of production lines or in component materials, for example, at an initial stage of factory production.

As shown in FIG. 1, the first through sixth terminals 28a-28f of the concentration measuring device 1 contact the ends 25b, 26b of the working and counterpart electrodes 25, 26, the first through third leads 28A-28C of the attribute information output section 28, and the fourth lead 29A of the correction information output section 29 (see FIG. 8A) when the biosensor 2 is attached to the concentration measuring device 1.

The switch unit 11 includes first-sixth analog switches 11a-11f. Each analog switch 11a-11f is separately turned on and off by the control unit 18. By operation of the respective analog switches 11a-11f, each of the terminals 10a-10f is selectively connected to the voltage applying unit 12 or to the electric current measuring unit 13.

The voltage applying unit 12 applies a voltage across the working electrode 25 and the counterpart electrode 26, across the second lead 28B and the first or third lead 28A, 28C, or across the third lead 28C and the fourth lead 29A. The voltage applying unit 12 comprises a direct-current power supply, such as a dry cell and a rechargeable battery.

The electric current measuring unit 13 measures the electric current flowing through a circuit formed by the voltage applying unit 12 and the biosensor 2.

The storage unit 14 stores data about the calibration curves, the measurement standard of the concentration measuring device 1, and the resistance preset for the fourth lead 29A, for example.

The detection unit 15 detects whether or not the biosensor 2 is attached to the concentration measuring device and whether or not a sample liquid is supplied to the reagent part 27, based on the current measured by the electric current measuring unit 13. Further, the detection unit 15 detects the measurement standard information and calibration curve selection information, based on the attribute information from the attribute information output section 28 and the correction information from the correction information output section 29.

The calibration curve selection unit 16 determines the calibration curve suitable for the sensitivity of the biosensor 2 based on the calibration curve selection information.

The judging unit 17 judges, based on the measurement standard information, whether or not the measurement standard matches that of the concentration measuring device 1.

The control unit 18 controls the operation of the switch unit 11 and the voltage applying unit 12. More specifically, the control unit 18 determines whether or not a voltage need be applied across the working and counterpart electrodes 25, 26 for example, and whether or not a voltage need be applied to desired points in the attribute information output section 28 and the correction information output section 29.

The calculating unit 19 calculates the concentration of the specific component in the sample liquid based on the responsive current measured by the electric current measuring unit 13 and the calibration curve determined by the calibration curve selection unit.

Each of the storage unit 14, the detection unit 15, the calibration curve selection unit 16, the judging unit 17, the control unit 18 and the calculating unit 19 may be constituted by a CPU and a memory such as ROM and RAM. Alternatively, all the units may be constituted by a single common CPU and a plurality of memories connected thereto.

Next, the operation of the concentration measuring device 1 is described with reference to FIGS. 6 through 9.

Figure 6:
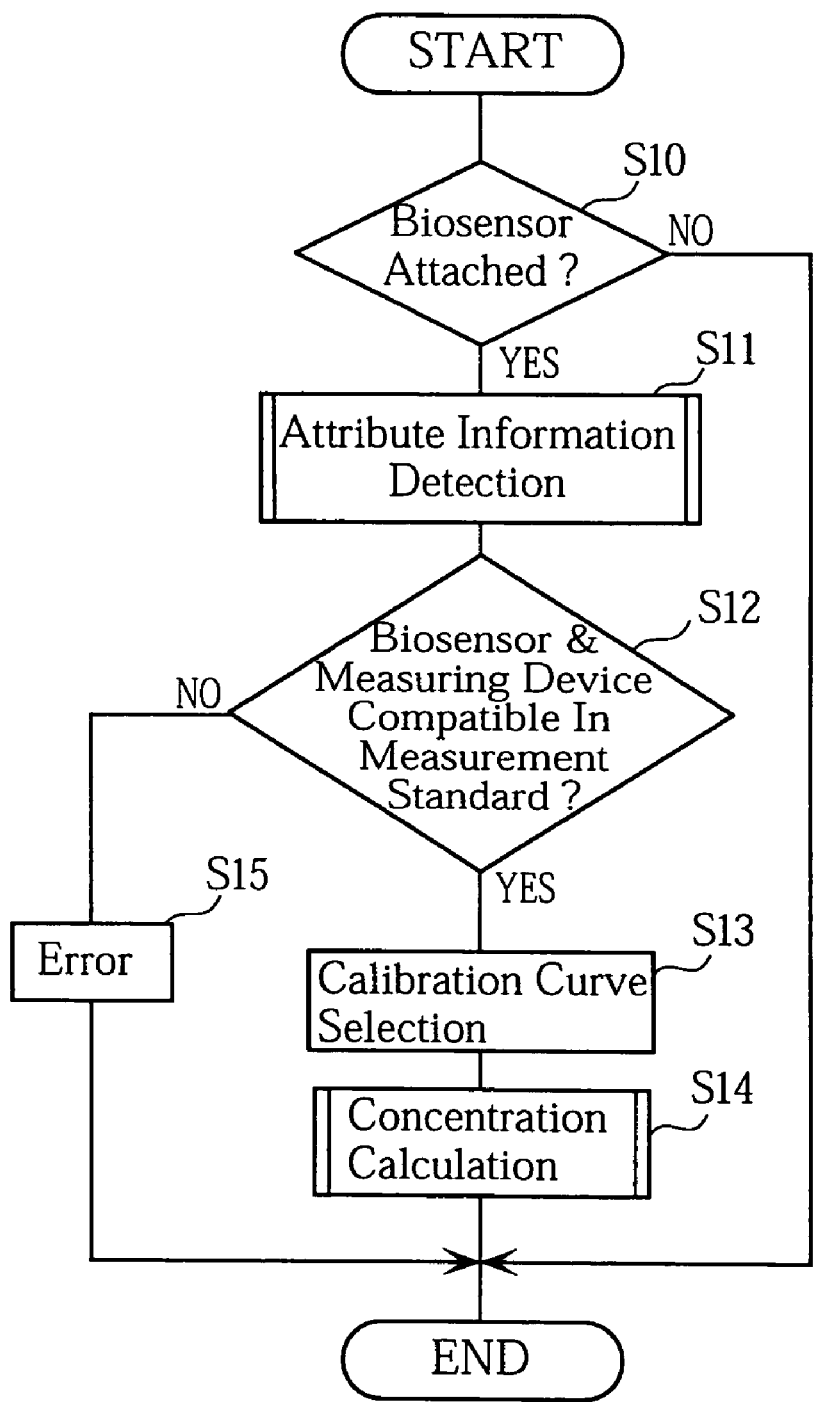
FIG. 6 is a flowchart showing the concentration measuring operation of the concentration measuring device according to the first embodiment of the present invention.

As shown in FIG. 6, the detection unit 15 first detects whether or not the biosensor 2 is attached to the concentration measuring device 1 (S10). To determine whether or not the biosensor 2 is attached, use is made of a detection sensor such as an optical sensor or a pressure sensor, or of the first through fourth leads 28A-28C, 29A.

When the detection unit 15 detects that the biosensor 2 is attached to the concentration measuring device 1 (S10: YES), the attribution information of the biosensor is checked (S11).

Figure 7:
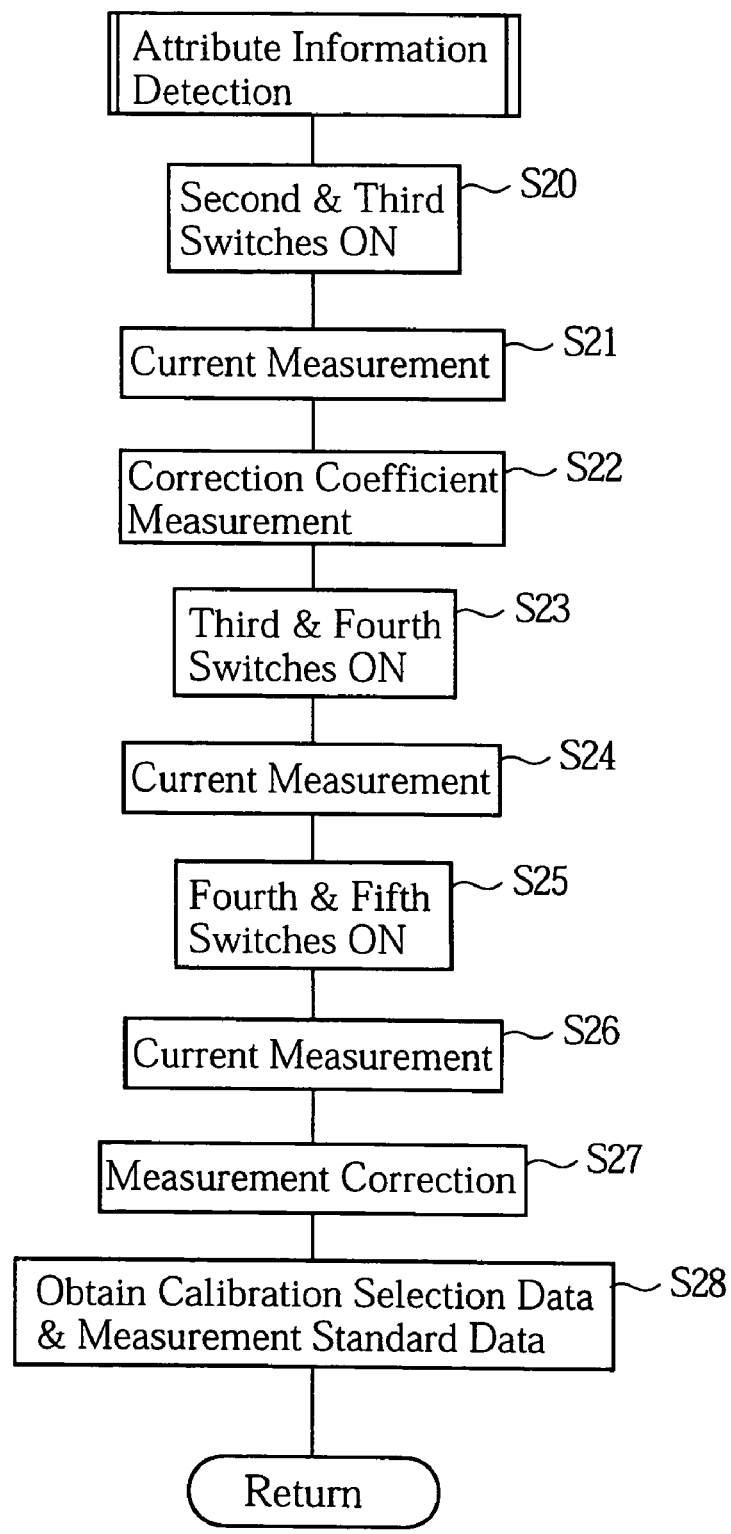
FIG. 7 is a flowchart showing the attribute information identification process.
Figure 8A:
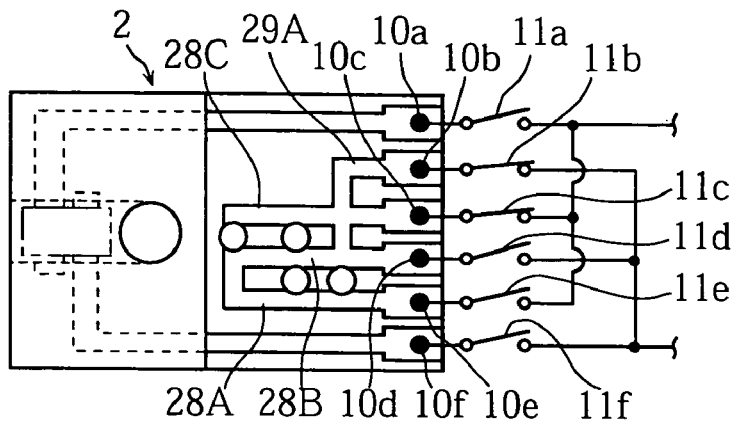
FIGS. 8A-8D are plan views illustrating the switching patterns of the analog switch.

As shown in FIGS. 7 and 8A, in the attribute information checking, the control unit 18 directs that the second and third switches 11b, 11c are switched on (S20). Next, a voltage is applied across the third and fourth leads 28C, 29A to measure the current flowing at the third and fourth leads 28C, 29A by the electric current measuring unit 13 (S21). Then, based on the current measured in S21, the detection unit 15 determines how much the actual resistance of the fourth lead 29A deviates from the preset resistance, and then calculates a compensation coefficient (S22).

Figure 8B:
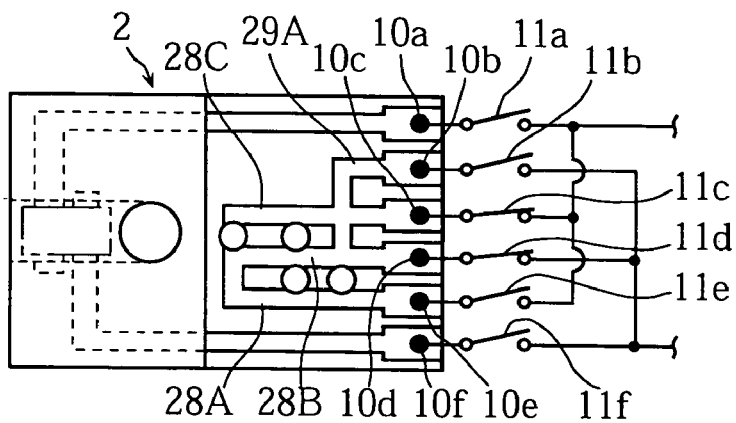
Figure 8C:
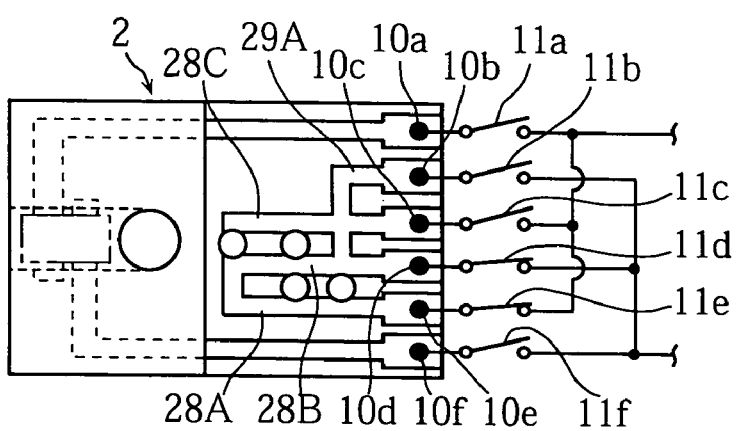

As shown in FIGS. 7 and 8B, the control unit 18 turns on only the third and fourth analog switches 11c, 11d (S23). Then, a voltage is applied across the second and third leads 28B, 28C, and the current measuring unit 13 measures the current flowing at the second and third leads 28B, 28C (S24). Similarly, as shown in FIGS. 7 and 8C, the fourth and fifth analog switches 11d, 11e are turned on by the control unit 18 (S25) for measuring the current flowing at the first and second leads 28A, 28B by the electric current measuring unit 13 (S26).

As shown in FIG. 7, the detection portion 15 corrects the measured values in S24 and S26 (or the calculated values based on the measured values) according to the compensation coefficient obtained at S22 (S27), and obtains, based on the corrected values, the calibration curve selection information and the measurement standard information (S28).

Next, the judging unit 17 determines whether or not the measurement standard of the biosensor 2 is one of the measurable standards for the concentration measurement device 1 (S12). If the concentration measuring device 1 is designed to cope with only one measurement standard, it is determined whether or not the sole measurement standard is the same as that of the biosensor 2.

If the judging unit 17 determines that the measurement standard of the biosensor 2 is not compatible with that of the concentration measurement device 1 (S12:NO), error handling is performed (S15). In this case, the concentration measurement with the current biosensor 2 is not performed, and the user is notified of the error by audio or visual means, for example.

On the other hand, if the judging unit 17 determines that the measurement standard of the biosensor 2 is compatible with the measurement standard of the concentration measuring device 1 (S12:YES), the calibration curve selection unit 16 selects, based on the calibration curve selection information, a calibration curve suitable for the biosensor 2 from the calibration curves stored in the storage unit 14 (S:13).

Figure 8D:
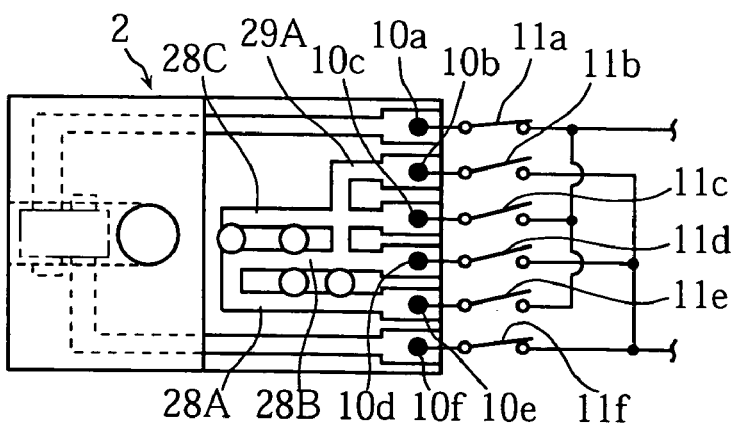
Figure 9:
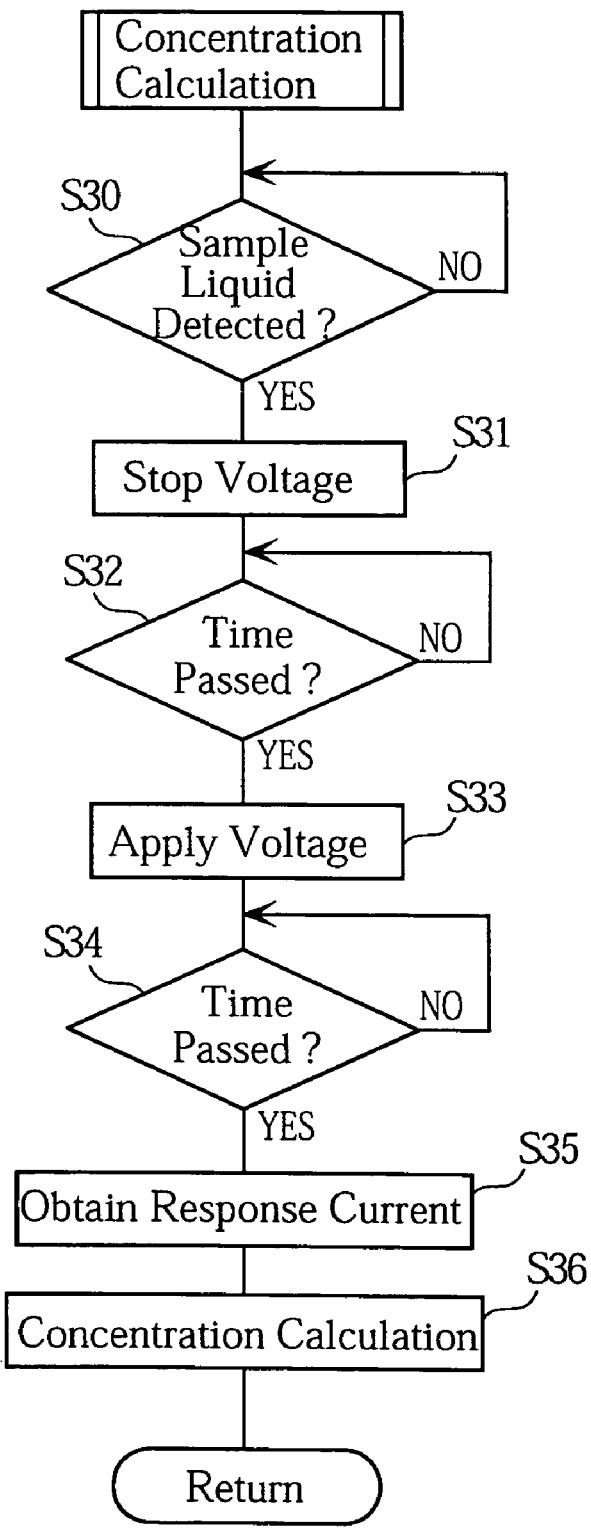
FIG. 9 is a flowchart showing the concentration calculating process.

Next, the concentration measurement process is performed according to the flowchart shown in FIG. 9 (S14). In a concentration calculation process, the detection unit 15 detects whether or not the reagent part 27 of the biosensor 2 is supplied with a sample liquid (S30). More specifically, the detection unit 15 compares the measured current by the electric current measuring unit 13 with a predetermined threshold when the first and sixth analog switches 11a, 11f only are turned on as shown in FIG. 8D. If the reagent part 27 is supplied with a sample liquid, the reagent part 27 is dissolved by the sample liquid to form a liquid phase reaction system. In the liquid phase reaction system, the specific component in the sample liquid is oxidized (or deoxidized), while an electron carrier is deoxidized (or oxidized). Consequently, when a voltage larger than a predetermined value is applied to the reagent part 27, the electron carrier is oxidized (or deoxidized), which generates an oxidation current (or a deoxidation current). Therefore, the electric current measuring unit 13 can detect that the reagent part 27 undergoes a proper reaction, that is, the reagent part 27 is supplied with the sample liquid, based on the measurement of the oxidation current (or the deoxidation current).

As shown in FIG. 9, if the detection unit 15 determines that no sample liquid is supplied (S30:NO), the determination process of S30 is repeated until the supply of a sample liquid is detected (S30:YES). At this time, an error processing may be performed if a predetermined period of time has passed after the biosensor 2 is attached, or if the supply of a sample liquid has not been detected after a predetermined number of determinations are performed.

When the detection unit 15 determines that the sample liquid is supplied (S30:YES), the voltage application to the reagent part 27 is stopped (S31). For stopping the application of voltage, the control unit 18 turns off the analog switches 11a, 11f based on the information from the detection unit 15.

Next, the control unit 18 determines whether or not the predetermined period of time has passed after the voltage application (S32). If the control unit 18 determines that the predetermined period of time has not passed (S32:NO), the determination of S32 is repeated until the unit determines that the predetermined period of time has passed (S32:YES). Since no voltage is applied to the reagent part 27 during the predetermined period of time, the deoxidized (or oxidized) electron carriers accumulate in the reagent part 27.

If the control unit 18 determines that the predetermined period of time has passed (S32:YES), the control unit 18 closes the analog switches 11a, 11f again to apply voltage to the liquid phase reaction system (S33).

The control unit 18 further determines whether or not a predetermined period of time has passed after the voltage application (S:34). If the control unit 18 determines that the predetermined period of time has not passed (S34:NO), the determination of S34 is repeated until the unit determines that the predetermined period of time has passed (S34:YES). Since a voltage is applied to the liquid phase reaction system during the predetermined period of time, the electron carriers are oxidized (or deoxidized). Consequently, the electrons are transferred between the liquid phase reaction system and the working electrode 25, and the electric current measuring unit 13 measures the response current. The response current continues to be measured and monitored by the detection unit 15.

When the control unit 18 determines that the predetermined period of time has passed (S34:YES), the calculating unit 19 obtains the current response current measured by the electric current measuring unit 13 from the detection unit 15 (S35). Further, the calculating unit 19 calculates the concentration of the specific component in the sample liquid (S36). The concentration calculation is performed by using the selected calibration curve against which the response current (or response voltage converted from the current in accordance with predetermined rules), obtained after a predetermined period of time has passed from the re-application of the voltage (S33 in FIG. 9), is checked.

As shown in FIG. 6, when the concentration measurement (S14) or the error processing (S15) is completed or the detection unit 15 determines that the biosensor 2 is not attached (S10:NO), the concentration measurement is terminated.

Other preferred embodiments of the present invention will be described below with reference to the accompanying drawings. In the figures referred below, the elements identical or similar to those of the first embodiment are designated by the same reference signs, and overlapping descriptions about the elements are omitted.

FIGS. 10A through 10D illustrate a second embodiment of the present invention. In the biosensors 3A-3C, desired attribute information can be output by selecting at least one of the location and the area size for forming the attribute information output sections 30A-30C. As described above, the attribute information may include calibration curve selection information (the sensor sensitivity) and measurement standard information. The biosensors 3A-3C are provided with at least one of these data.

The attribute information output sections 30A-30C of the biosensors 3A-3C are formed between the end 25b of the working electrode 25 and the end 26b of the counterpart electrode 26. The attribute information output unit 30A shown in FIG. 10A is brought into contact with second through fourth terminals 40b-40d of the concentration measuring device when the biosensor 3A is attached to the concentration measuring device. The attribute information output unit 30B shown in FIG. 10B is formed so as to contact the third and fourth terminals 40c, 40d but not to contact the second terminal 40b in attaching the biosensor 3B. The attribute information output unit 30C shown in FIG. 10C is formed so as to contact the second and third terminals 40b and 40c but not to contact the fourth terminal 40d in attaching the biosensor 3C. Of course, as shown in FIG. 10D, the concentration measuring device can recognize attribute information of a biosensor 3D provided with no attribute information output section.

Figure 11A:
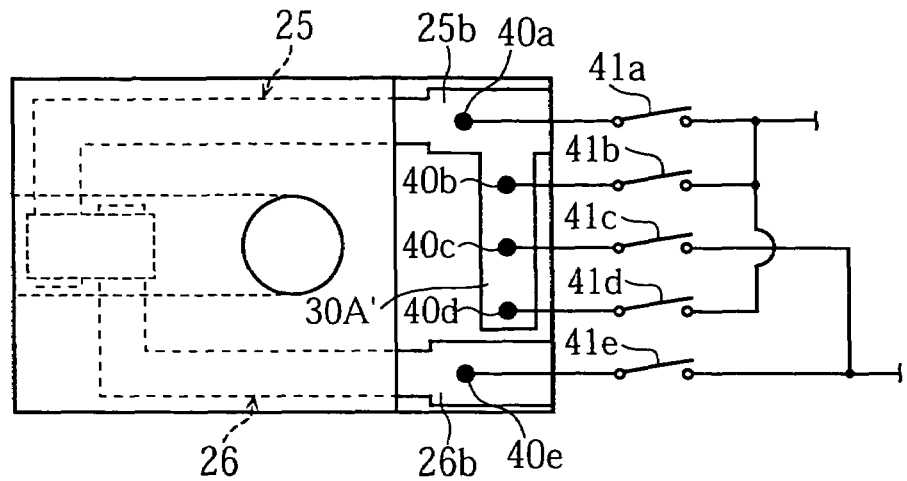
FIGS. 11A-11C are plan views illustrating a modification example of the biosensor shown in FIGS. 10A-10C.
Figure 11B:
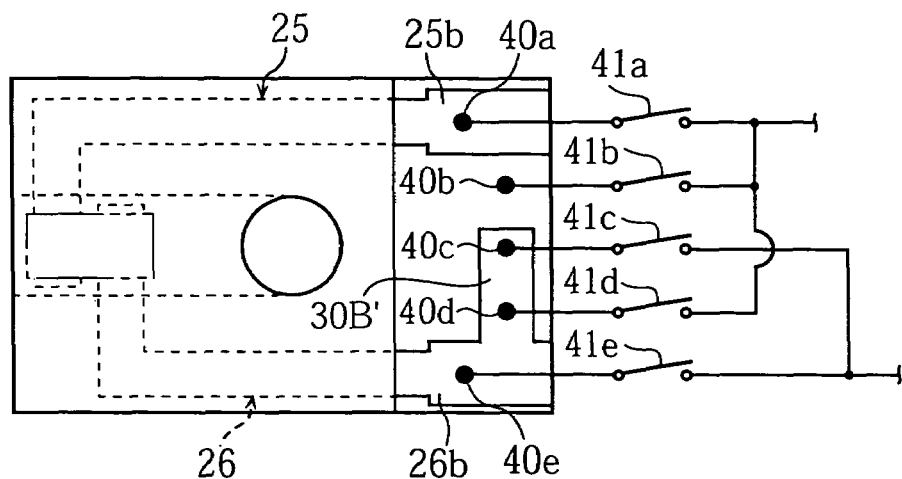
Figure 11C:
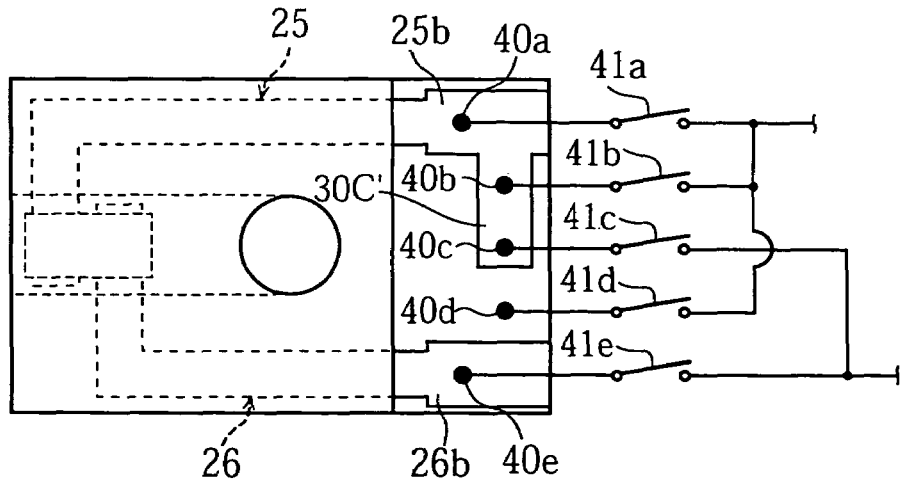

As shown in FIG. 11A-11C, attribute information output sections 30A'-30C may be integrally formed with either of the working electrode 25 and the counterpart electrode 26.

After the biosensor 3A-3C is inserted into the concentration measuring device, the detection of the attribute information is performed by turning the first and fifth analog switches 41a, 41f off, turning the third analog switch 41c on, and turning one of the second and fourth analog switches 41b and 41d on while turning the other off.

Figure 12A:
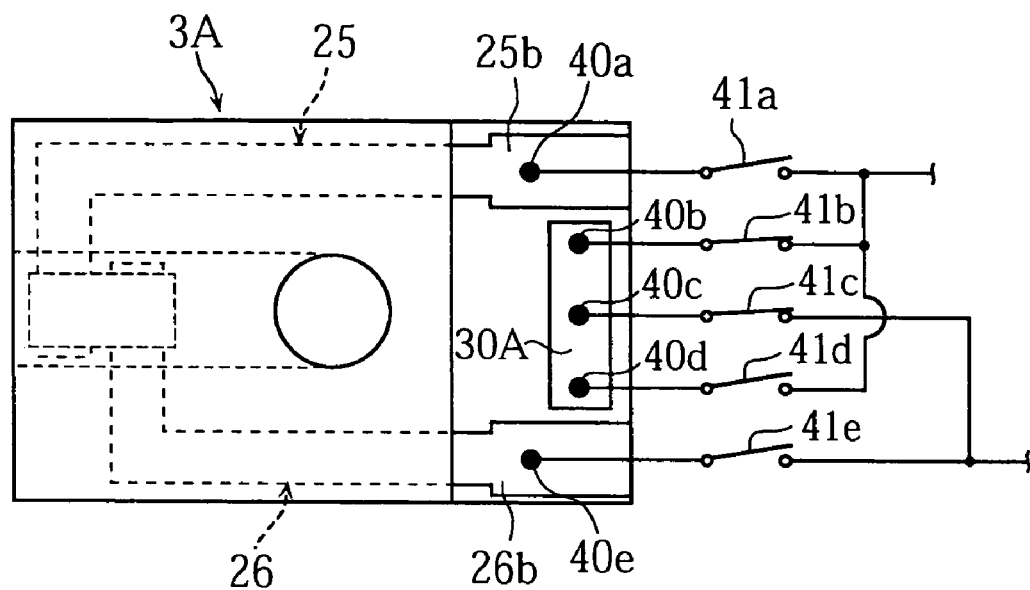
FIGS. 12A and 12B are plan views illustrating the switching patterns of the analog switch in the second embodiment of the present invention.
Figure 12B:
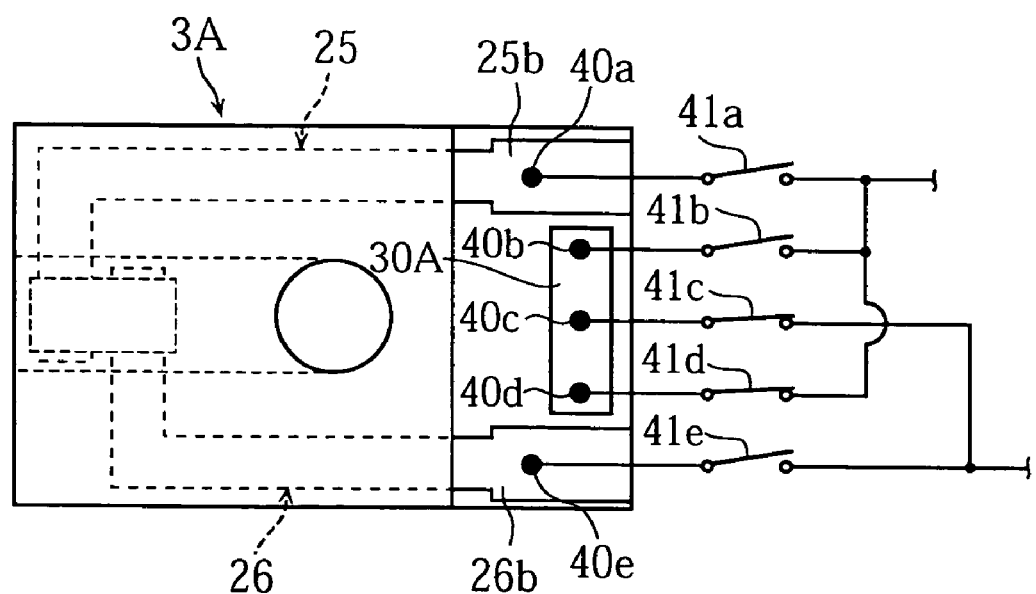

Detail description for the method of recognizing the attribute information will be given below with the biosensor 3A in FIG. 10A taken as an example. First, as shown in FIG. 12A, the second and third analog switches 41b, 41c are turned on. Since the attribute information output section 30A is arranged between the second and third terminals 40b, 40c, these terminals are shorted. Then, the third and fourth analog switches 41c, 41d are turned on. As shown in FIG. 12B, the attribute information output section 30A is arranged between the third and fourth terminals 40c, 40d, and therefore the terminals 40c, 40d are shorted. Accordingly, there is generated a signal indicating that the second and third terminals 40b, 40c as well as the third and fourth terminals 40c, 40d are shorted in the biosensor 3A shown in FIG. 10A. Such a signal may be obtained by causing the detection unit 15 to detect whether or not a current is measured by the electric current measuring unit 13 (see FIG. 1).

According to the same recognizing method as described above, in the biosensor 3B shown in FIG. 10B, there is generated a signal indicating that the second and third terminals 40b, 40c are open while the third and fourth terminals 40c, 40d are shorted. In the biosensor 3C shown in FIG. 10C, there is generated a signal indicating that the second and third terminals 40b, 40c are shorted while the third and fourth terminals 40c, 40d are open. In the biosensor 3D shown in FIG. 10D, there is generated a signal indicating that the second and third terminals 40b, 40c as well as the third and fourth terminals 40c, 40d are open.

In this way, it is possible to output the desired information selected from the four kinds of information by the selective use of the biosensors 3A through 3D differing in location and area size (including a case where no attribute information output section is provided) for forming the attribute information output sections 30A-30C.

The attribute information output section for outputting an open-short signal can be formed by preparing a strip conductor or resistor set connection-breakable parts and then disconnecting or leaving the parts depending on kinds of information to be output.

The attribute information output sections 30A-30C can output more kinds of information by setting a plurality of resistances. When the second and third terminals 40b, 40c or the third and fourth terminals 40c, 40d are shorted, two (or more) kinds of short-related outputs can be separately used to indicate: shorted and having a greater resistance; or shorted and having a smaller resistance. When many kinds of information are available, the biosensors 3A-3C can output both the measurement standard information and the calibration curve selection information without causing any trouble. Further, when the biosensors 3A-3C are used together with a correction chip for calibration curve selection, the attribute information output sections 30A-30C can be arranged to output information that one of the biosensors 3A-3C is attached to the concentration measuring device.

The resistance can be adjusted by changing the cross-sectional area (thickness or width) of the attribute information output sections 30A-30C, the length of the sections 30A-30C, or the material for making the sections 30A-30C.

Figure 13:
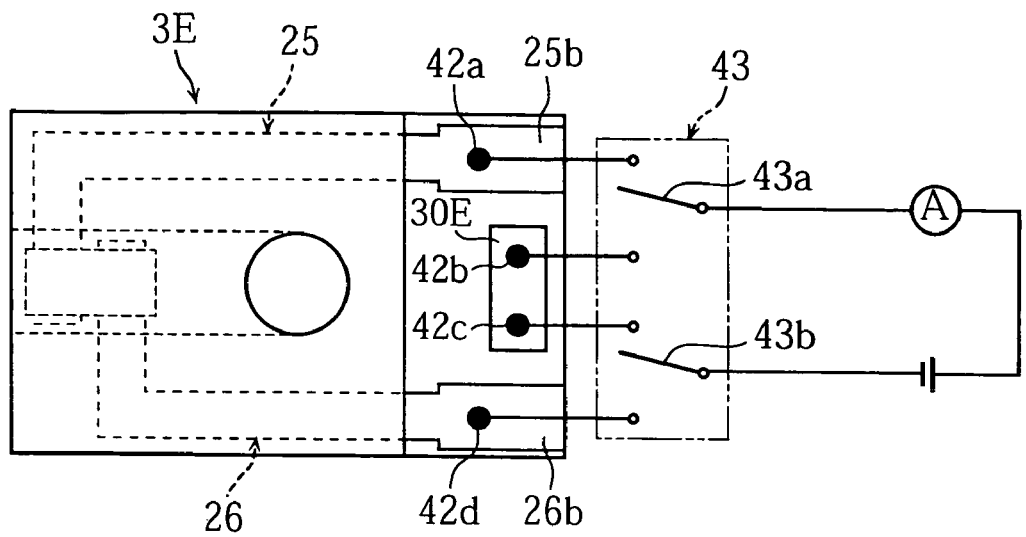
FIG. 13 is a plan view showing a third embodiment of the present invention.

FIG. 13 illustrates a third embodiment of the present invention. The concentration measuring device includes first-fourth terminals 42a-42d and a switching unit 43. The switching unit 43 includes two analog switches 43a, 43b. In this arrangement, the analog switches 43a, 43b are operated to selectively provide a state where a voltage is applied across the first and fourth terminals 42a, 42d and a state where a voltage is applied across the second and third terminals 42b, 42c.

A biosensor 3E includes an attribute information output section 30E formed between the ends 25b, 26b of the working and counterpart electrodes 25, 26. The attribute information output section 30E has a resistance corresponding to the attribute information to be output. By measuring the current (resistance of the attribute information output section 30E) flowing at the second and third terminals 42b, 42c, the concentration measuring device can detect the attribute information of the biosensor 3E such as calibration curve selection information and measurement standard information.

When the concentration measuring device is provided with three calibration curves for example, the first calibration curve may correspond to a resistance of 2000-2600Ω of the attribute information output section 30E, the second calibration curve may correspond to a resistance of 2600-3000Ω of the attribute information output section 30E, and the third calibration curve may correspond to a resistance of 3000-3800Ω of the attribute information output section 30E.

The attribute information to be output may include measurement standard information in addition to the calibration curve selection information. In the above-mentioned case, 2000-2200Ω, 2600-2800Ω and 3200-3400Ω may correspond to first measurement standard information, 2200-2400Ω, 2800-3000Ω and 3400-3600Ω may correspond to second measurement standard information, and 2400-2600Ω, 3000-3200Ω and 3600-3800Ω may correspond to third measurement standard information.

When it is arranged that the contents of the attribute information can be distinguished by resistance, the resistances to be adopted may be taken from only one of a plurality of predetermined resistance ranges (2000-4000Ω, 4000-6000Ω, etc.). In such an instance, the concentration measuring device may be arranged to determine within which resistance range the resistance of the attribute information output section 30E falls. Based on this determination, the concentration measuring device can further determine whether or not the instrument provided with the section 30E is a biosensor (i.e., the instrument can output any information for enabling the concentration calculation).

Of course, the number of the calibration curves is not limited to three. The resistances described above are only for example's sake. The resistance range is not limited as long as the relationship between the calibration curve selection information and the calibration curve to be selected is well-defined and so is the relationship between the measurement standard and the measurement standard information.

The resistance of the attribute information output section 30E can be adjusted by changing the amount of added conductive powder or the thickness and size of the attribute information output section 30E. The attribute information output section 30E of the biosensor 3E can be simultaneously formed with the working and counterpart electrodes 25, 26 under circumstances where biosensors 3E having the substantially same sensitivity can be stably supplied (i.e. where production lines are stably operated with the production conditions and the materials standardized). Specifically, a mask for forming the working electrode 25 and counterpart electrode, 26 is formed with an opening corresponding to the attribute information output section 30E. When this opening is rectangular, for example, the width or length of the opening may be varied for adjusting the resistance of the attribute information output section 30E. If the sensitivity of the sensor is anticipated accurately, the shape of the opening can be uniquely determined. Consequently, each production line can utilize the mask having an opening suitable for the production line. Since there is no need to provide an additional production line for producing correction chips in addition to the sensor production line, the production cost can be relatively low.

The resistance adjustment of the attribute information output section 30E may be performed at a last stage after the overall characteristics of biosensor's sensitivities are grasped by sampling a number of biosensors 3E among concentration measuring sensors produced under the same conditions. This is an effective means under such circumstances that the sensitivity of the biosensors is unpredictable because of change in materials or in design of production lines, e.g. in an initial stage for launching the production lines. The resistance adjustment may be performed by providing a resistor element of a known resistance after the working electrode 25, the counterpart electrode 26 and a conductive part are formed. The adjustment may also be performed by modifying the surface state of the conductive part. The modification may be performed by forming an oxidized layer or a nitride layer by CVD, laminating a resistance material and a resistance material by PVD, implanting metal ions into the conductive part, or laser trimming. These methods can provide the attribute information output portions having a variety of resistances by adjusting the surface modification time. This enables prompt action to cope with the change in materials or in design of production lines.

Figure 14:
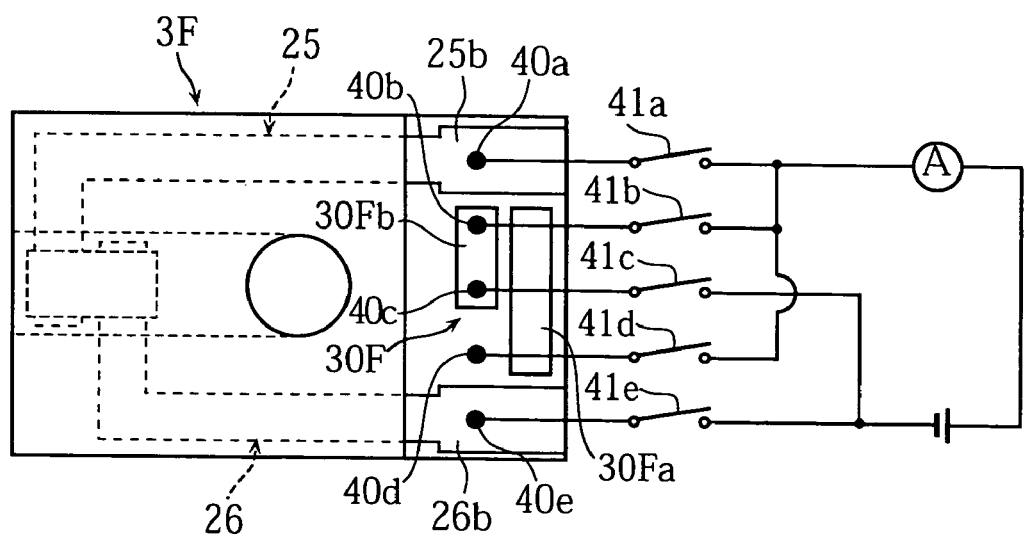
FIG. 14 is a plan view showing a fourth embodiment of the present invention.

FIG. 14 shows a fourth embodiment of the present invention. A biosensor 3F includes an attribute information output section 30F consisting of first and second individual information parts 30Fa, 30Fb. In this arrangement, the two individual information parts 30Fa, 30Fb can be used to output open-short information between the second and the third terminals 40b, 40c as well as the third and the fourth terminals 40c, 40d. In this manner, it is possible to output more information than when the attribute information output section consists of only one output part.

Figure 15A:
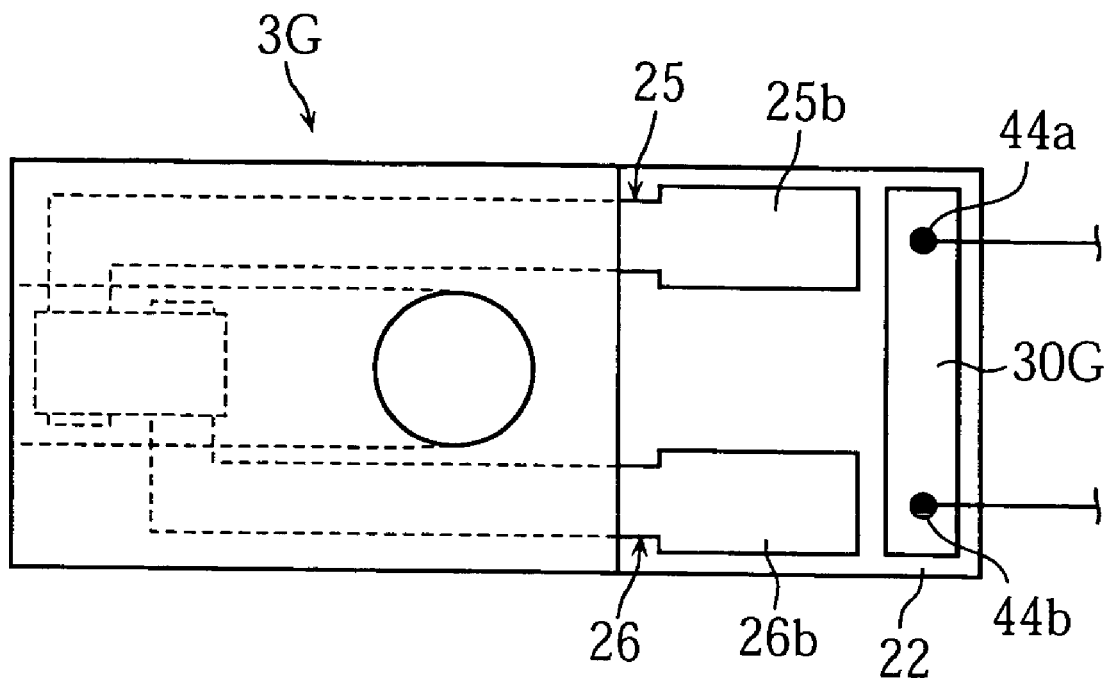
FIGS. 15A and 15*b* are plan views showing a fifth embodiment of the present invention.
Figure 15B:
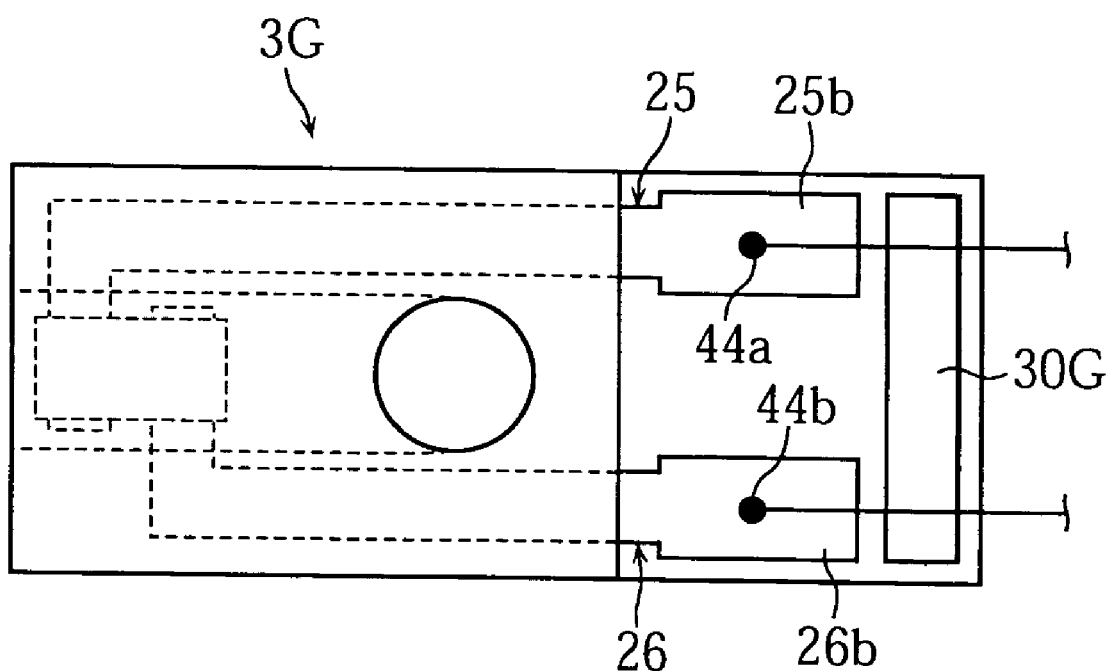

FIGS. 15A and 15B show a fifth embodiment of the present invention. A biosensor 3G includes an attribute information output portion 30G arranged nearer to an end (attaching end) in relation to the ends 25b, 26b of the working and counterpart electrodes 25, 26. The attribute information output portion 30G formed in a strip extending widthwise of the substrate 22. The output portion 30G outputs attribute information distinguished depending on the resistance of the output portion 30G.

The concentration measuring device includes first and second terminals 44a, 44b. As shown in FIG. 15A, the first and second terminals 44a, 44b contact the attribute information output section 30G when the biosensor 3G is being attached to the concentration measuring device. As shown in FIG. 15B, when the attachment of the biosensor 3G to the concentration measuring device is completed, the terminals contact the ends 25b, 26b of the working and counterpart electrodes 25, 26. Therefore, the concentration measuring device does not need to have any terminal for causing the biosensor 3G to contact the attribute information output section 30G. This simplifies the structure of the concentration measuring device and provides a cost advantage.

Figure 16A:
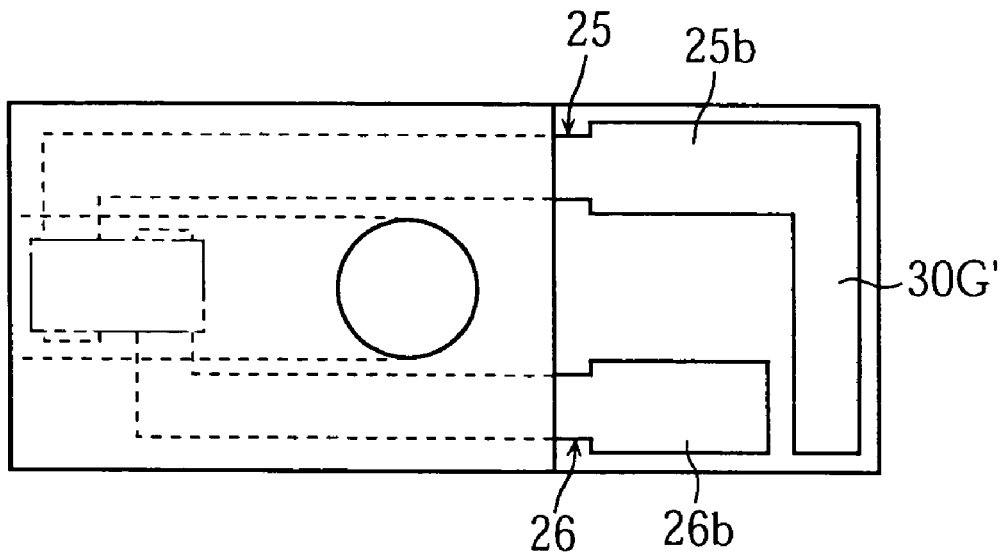
FIGS. 16A and 16B are plan views illustrating a modification example of the biosensor shown in FIGS. 15A and 15B.
Figure 16B:
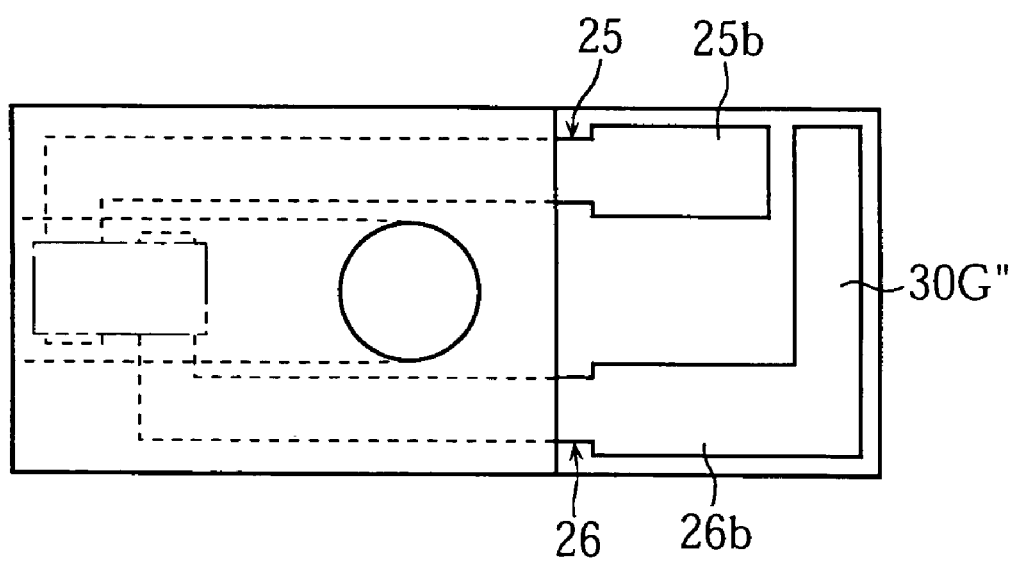

As shown in FIGS. 16A and 16B, the attribute information output portions 30G', 30G" may be formed integrally with the working electrode 25 or the counterpart electrode 26.

Figure 17A:
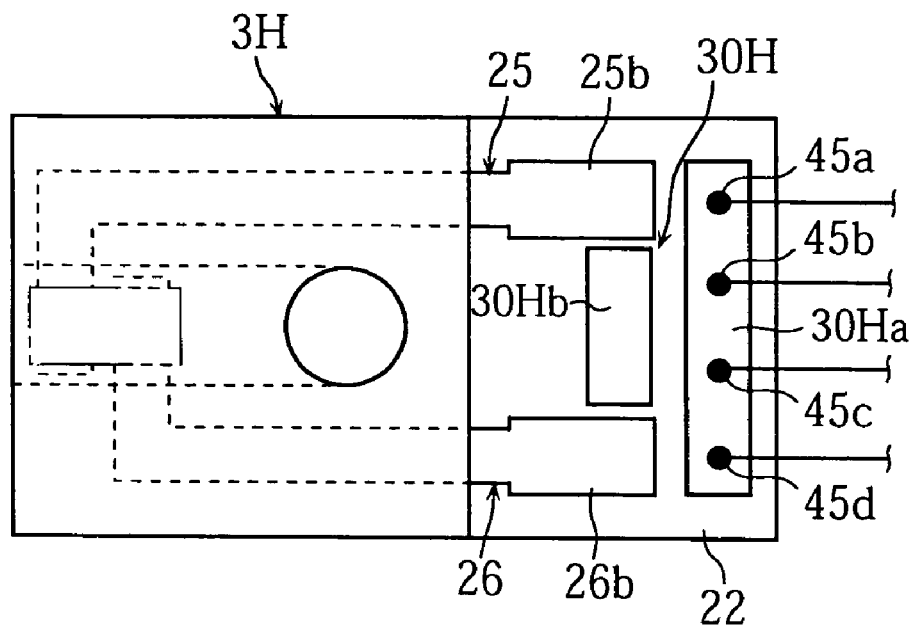
FIGS. 17A and 17B are plan views illustrating a sixth embodiment of the present invention.
Figure 17B:
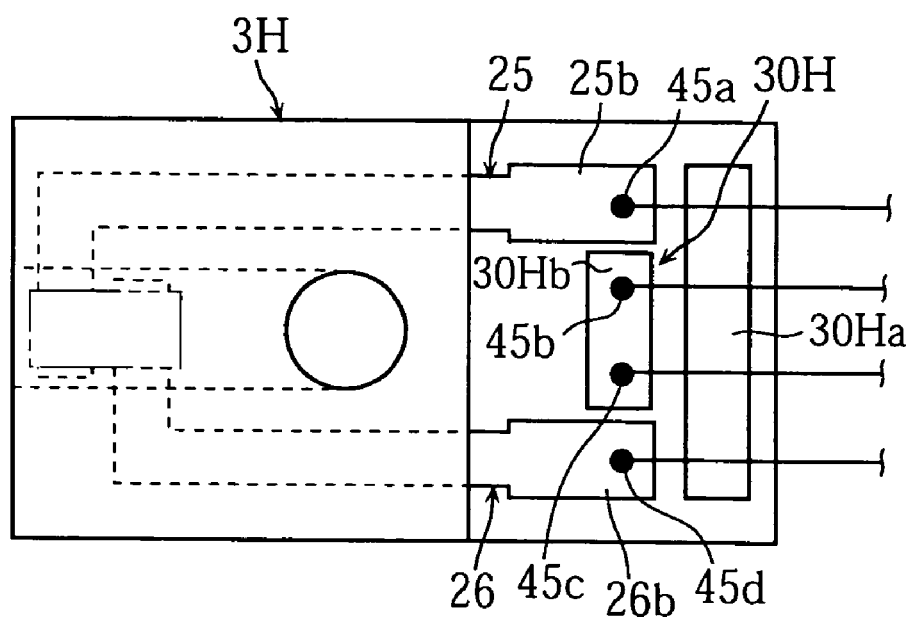

FIGS. 17A and 17B show a sixth embodiment of the present invention.

A biosensor 3H has an attribute information output section 30H including first and second individual information output sections 30Ha, 30Hb. The first individual information output section 30Ha is formed in the same portion as the attribute information output section 30G of the biosensor 3H shown in FIG. 15. The first individual information output section 30Ha is formed in a strip extending over substantially the entire width of the substrate 22. The second individual information output section 30Hb is formed between the ends 25b, 26b of the working and counterpart electrodes 25, 26. The second individual information output section 30Hb is shorter than the first individual information output section 30Ha. The first and second individual information output sections 30Ha, 30Hb are fabricated in the same production step and made of the same material, and therefore differ in resistance.

The concentration measuring device includes first-fourth terminals 45a-45d for the first and second individual information output sections 30Ha, 30Hb of the attribute information output section 30H. The first and the fourth terminals 45a, 45d contact the individual information output section 30Ha in attaching the biosensor 3H to the concentration measuring device. When the attachment of the biosensor 3H to the concentration measuring device is completed, these terminals contact the ends 25b, 26b of the working and counterpart electrodes 25, 26. The second and the third terminals 45b, 45c contact the individual information output section 30Ha in attaching the biosensor 3H to the concentration measuring device. When the attachment of the biosensor 3H to the concentration measuring device is completed, these terminals contact the individual information output section 30Hb.

In this arrangement, the first output section 30Ha outputs individual information when the biosensor 3H is being attached to the concentration measuring device, while the second output section 30Hb outputs individual information when the attachment of the biosensor 3H to the concentration measuring device is completed.

FIGS. 18A-18D show a seventh embodiment of the present invention.

A biosensor 3I has an attribute information output section 30I including first-third individual information output sections 30Ia-30Ic. The first-third individual information output sections 30Ia-30Ic are formed in the same region as the attribute information output section 30G. The first-third individual information output sections 30Ia-30Ic are formed in a strip extending widthwise of the substrate 22. The first-fourth terminals 45a-45d contact the first-third individual information output sections 30Ia-30Ic in attaching the biosensor 3I to the concentration measuring device.

This arrangement can output various kinds of information with the use of the first-third individual information output sections 30Ia-30Ic.

If the substrate 22 has a length L of 10 mm and a width W of 5 mm for example, it is difficult to set a dimension D between the ends 25b, 26b of the electrodes 25, 26 and the shorter end 22b of the substrate 22 to 5 mm or more. In this case, the width of each first-third individual information output section 30Ia-30Ic may be 1 mm or less.

The inventors of the present invention produced rectangular sample conductors by screen printing and then evaluated the production error based on the measurements of their resistance. The conductors were 25 mm in length and 15 μm in thickness, but their widths came in three types: 3 mm (type. 1), 2 mm (type. 2) and 1 mm (type. 3). 20 conductors were prepared for each type. The conductors were formed by placing a mask having an opening corresponding to the conductive part on a PET substrate, filling the opening with carbon ink, and then performing heat treatment.

The carbon ink was prepared to include carbon black powder (having a weight-average particle diameter of 5 μm or less) of 100 weight parts, polyvinyl butylenes of 25 weight parts as a binder resin, and butyl cellosolve acetate of 125 weight parts as a solvent. The heat treatment was performed for 30 minutes at 140° C.

The resistance was measured by applying a constant voltage of 500 mV across the longitudinal ends of the conductor surface with probes contacting the ends, and then performing a calculation based on the current according to Ohm's law. The results are shown in table 1.

TABLE 1

| | Carbon Resistance (Ω) | | |
|---|---|---|---|
| Sample NO. | Width 3 mm (Type 1) | Width 2 mm (Type 2) | Width 1 mm (Type 3) |
| 1 | 530 | 725 | 920 |
| 2 | 660 | 825 | 990 |
| 3 | 662 | 876 | 1090 |
| 4 | 685 | 904 | 1123 |
| 5 | 581 | 758 | 935 |
| 6 | 618 | 780 | 942 |
| 7 | 665 | 862 | 1059 |
| 8 | 589 | 816 | 1043 |
| 9 | 544 | 791 | 1038 |
| 10 | 577 | 773 | 969 |
| 11 | 617 | 902 | 1187 |
| 12 | 373 | 732 | 1091 |
| 13 | 517 | 731 | 945 |
| 14 | 414 | 695 | 976 |
| 15 | 776 | 908 | 1040 |
| 16 | 556 | 795 | 1034 |
| 17 | 720 | 898 | 1076 |
| 18 | 602 | 835 | 1068 |
| 19 | 518 | 761 | 1004 |
| 20 | 596 | 805 | 1014 |
| Avg. | 590 | 808.6 | 1027.2 |
| SD | 95.6 | 66.2 | 69.0 |
| C.V.(%) | 16.2 | 8.2 | 6.7 |

As understood from Table 1, the type. 1 of 3 mm width has a standard deviation (SD) much larger than the types. 2 and 3, which is smaller in width than type. 1. Similarly, the type. 1 has a relative standard deviation (C. V.) much larger than the types. 2 and 3. In light of this, it is preferable that the attribute information output section has a width of 2 mm or less. Particularly, as to the C.V. indicating relative differences, the differences lessen when the width is smaller. In this light, it is preferable that the width is 1 mm or less. Applying this to the biosensor 3I shown in FIG. 18, the biosensor can be formed so that the individual information output sections have approximately desired resistances. In other words, it is possible to produce individual information output sections 30Ia-30Ic capable of outputting individual information which are easily distinguished from each other.

As understood from the results shown in Table 1, the maximum value of type. 1 does not overlap the minimum value of type. 2, while the maximum value of type. 2 does not overlap the minimum value of type. 3. Therefore, three kinds of attribute information output sections of 1 mm, 2 mm, and 3 mm width can be distinguished from each other for selecting a calibration curve suitable for the sensitivity of the biosensor from the three kinds of calibration curves for example. Applying this to the biosensor 3G shown in FIG. 15, the attribute information output section 30G is formed to have one of the widths 1 mm, 2 mm and 3 mm, thereby ensuring that the most appropriate calibration curve for the sensitivity of the biosensor 2 is selected from the three kinds of calibration curves, for example. In this manner, only adjusting the width of the attribute information output section 30G can provide a biosensor 3G capable of outputting information needed for selection of the calibration curve or detection of the measurement standard.

FIGS. 19-22 show an eighth embodiment of the present invention.

Figure 19:
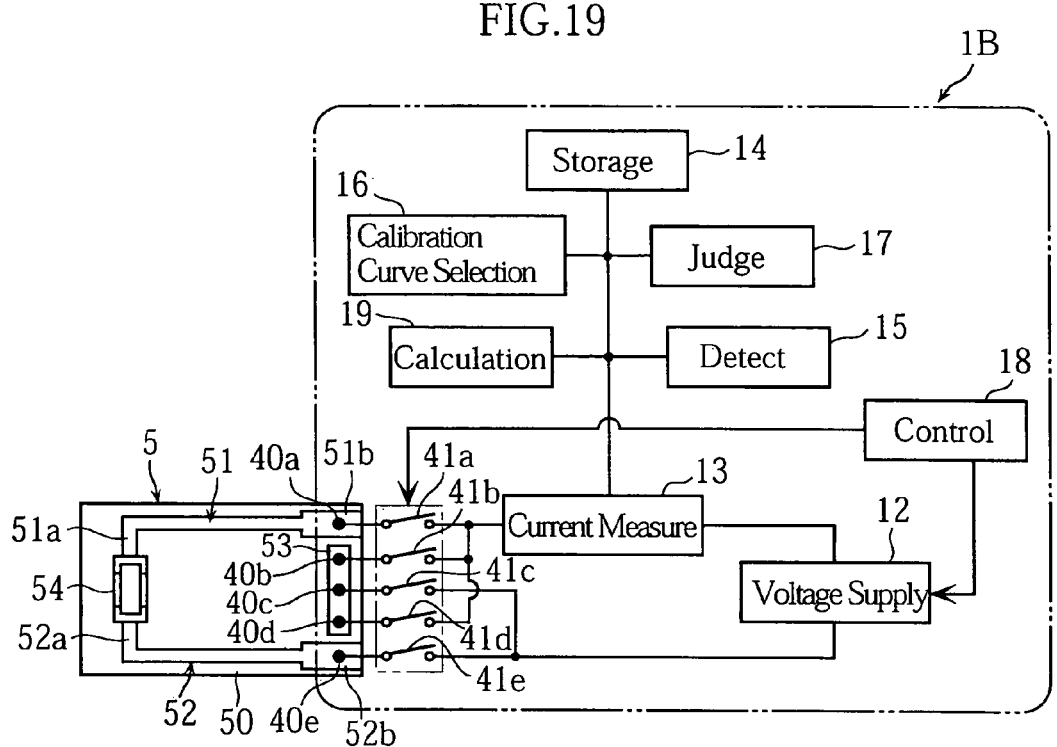
FIG. 19 is a schematic view showing a concentration measuring device with a correction chip according to an eighth embodiment of the present invention.
Figure 20:
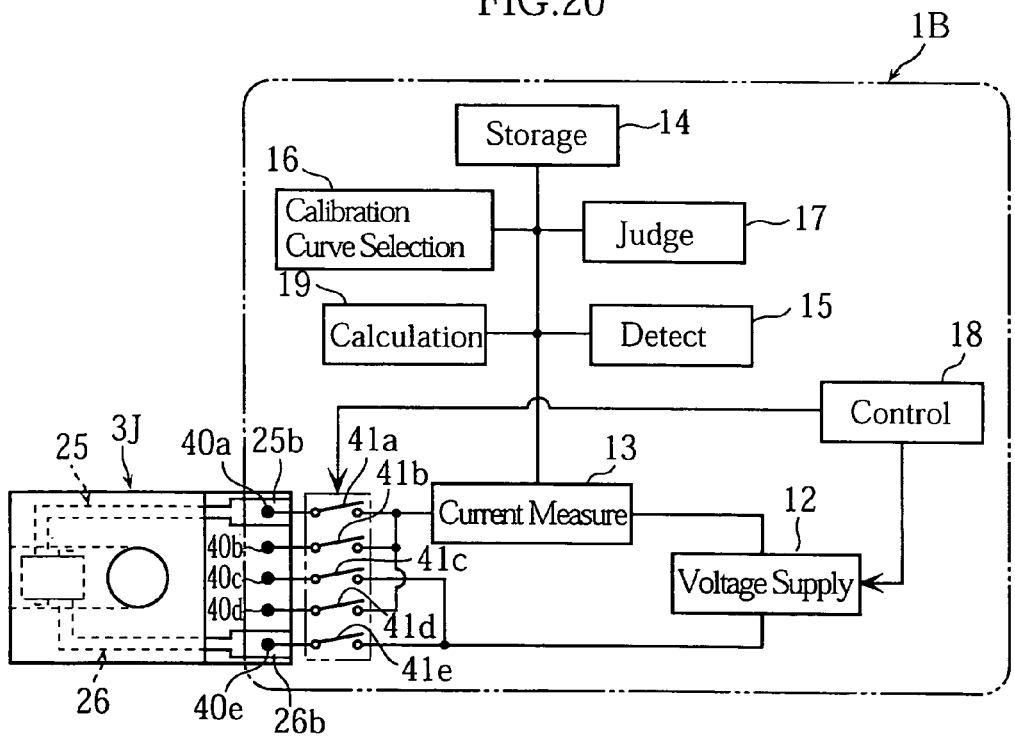
FIG. 20 is a schematic view showing the concentration measuring device with a biosensor according to the eighth embodiment of the present invention.

As shown in FIGS. 19 and 20, a concentration measurement device 1B first selects a calibration curve suitable for a biosensor 3J when a correction chip 5 is attached, and then performs concentration calculation based on the selected calibration curve when the biosensor 3J is attached. Therefore, the correction chip 5 and the biosensor 3J are used as a set. On the market, one correction chip 5 may be sold together with one lot of biosensors 3J.

Figure 21:
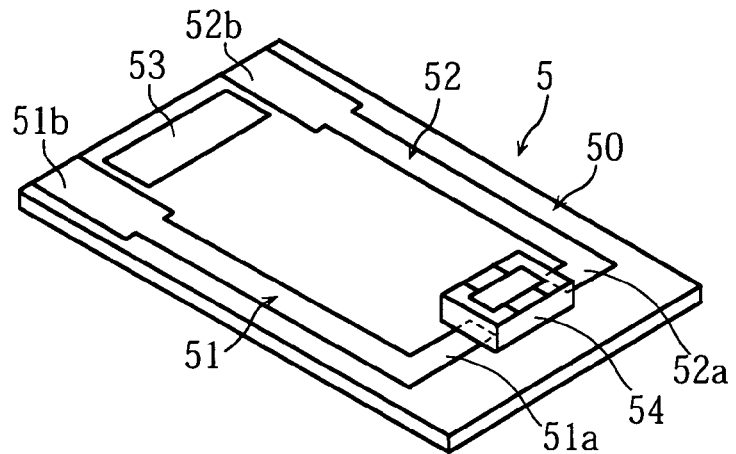
FIG. 21 is a perspective view of the correction chip shown in FIG. 19.

As shown in FIGS. 19 and 21, the correction chip 5 has a rectangle substrate 50 formed with a pair of electrodes 51, 52 and a measurement standard information output section 53. The paired electrodes 51, 52 include front ends 51a, 52a bridged by a chip resistor 54. The chip resistor 54 has a resistance corresponding to the sensitivity of the biosensor 3J. Therefore, the concentration measuring device 1B can select the most suitable calibration curve for the biosensor 3J based on a current flowing upon application of a constant voltage to the chip resistor 54 via the first and fifth terminals 40a, 40e. Of course, the electrodes 51, 52 may be bridged directly or by a resistance material to output calibration curve information corresponding to the resistance measured with use of the electrodes 51, 52.

The measurement standard information output section 53 extends widthwise of the substrate 50 between the ends 51b, 51b of the electrodes 51, 52. The output section 53 outputs information about a measurement standard applied to the biosensor 3J. When the correction chip 5 is attached to the concentration measuring device 1B, the output section 53 contacts the second through fourth terminals 40b-40d. Thus, the measurement standard information of the biosensor 3J can be obtained in accordance with a combination of open-short signals between the second and third terminals 41b, 41c and between the third and fourth terminals 41c, 41d by switching the analog switches 41b-41d. Of course, the measurement standard information is recognized by the output section 53 having a structure shown in FIGS. 10A through 10C, or without providing the output section 53, depending on desired measurement standard information.

Figure 22:
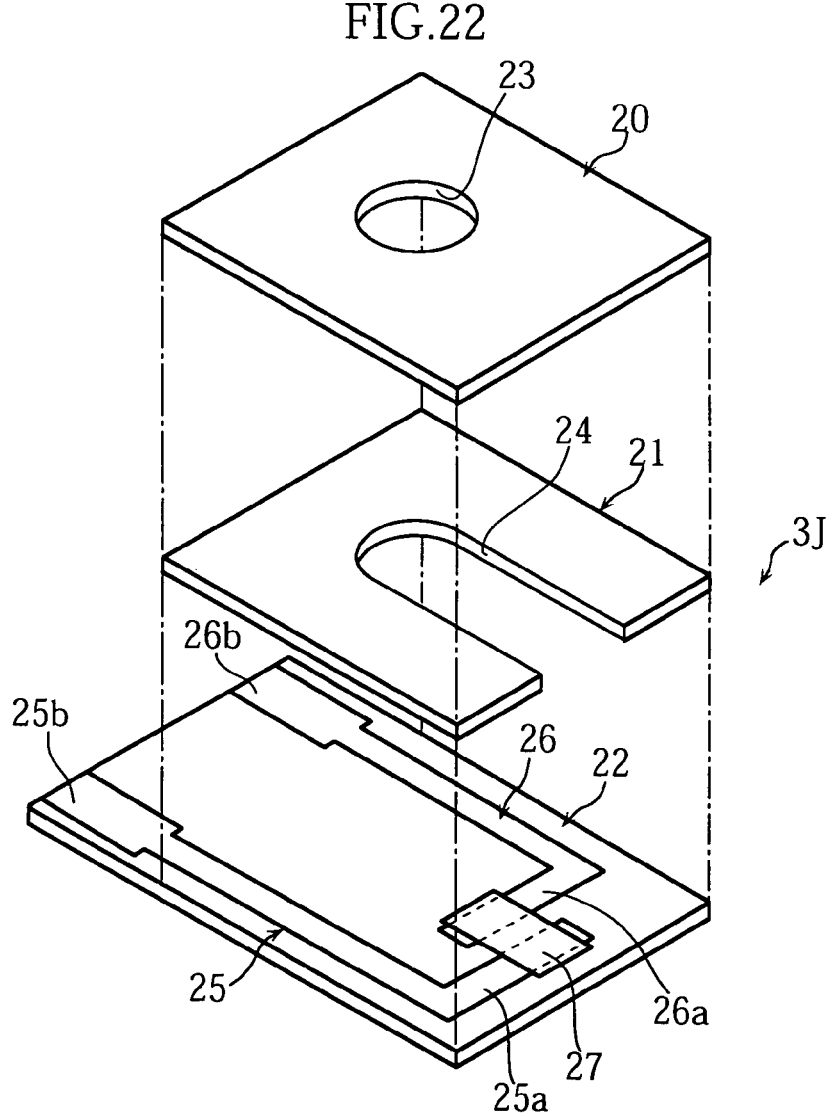
FIG. 22 is an exploded perspective view of the biosensor shown in FIG. 20.

As shown in FIGS. 20 and 22, the biosensor 3J has a structure similar to those of the above-described biosensors 2, 3A-3I but with no attribute information output section (see FIGS. 2, 10, 11-18) provided.

Figure 23:
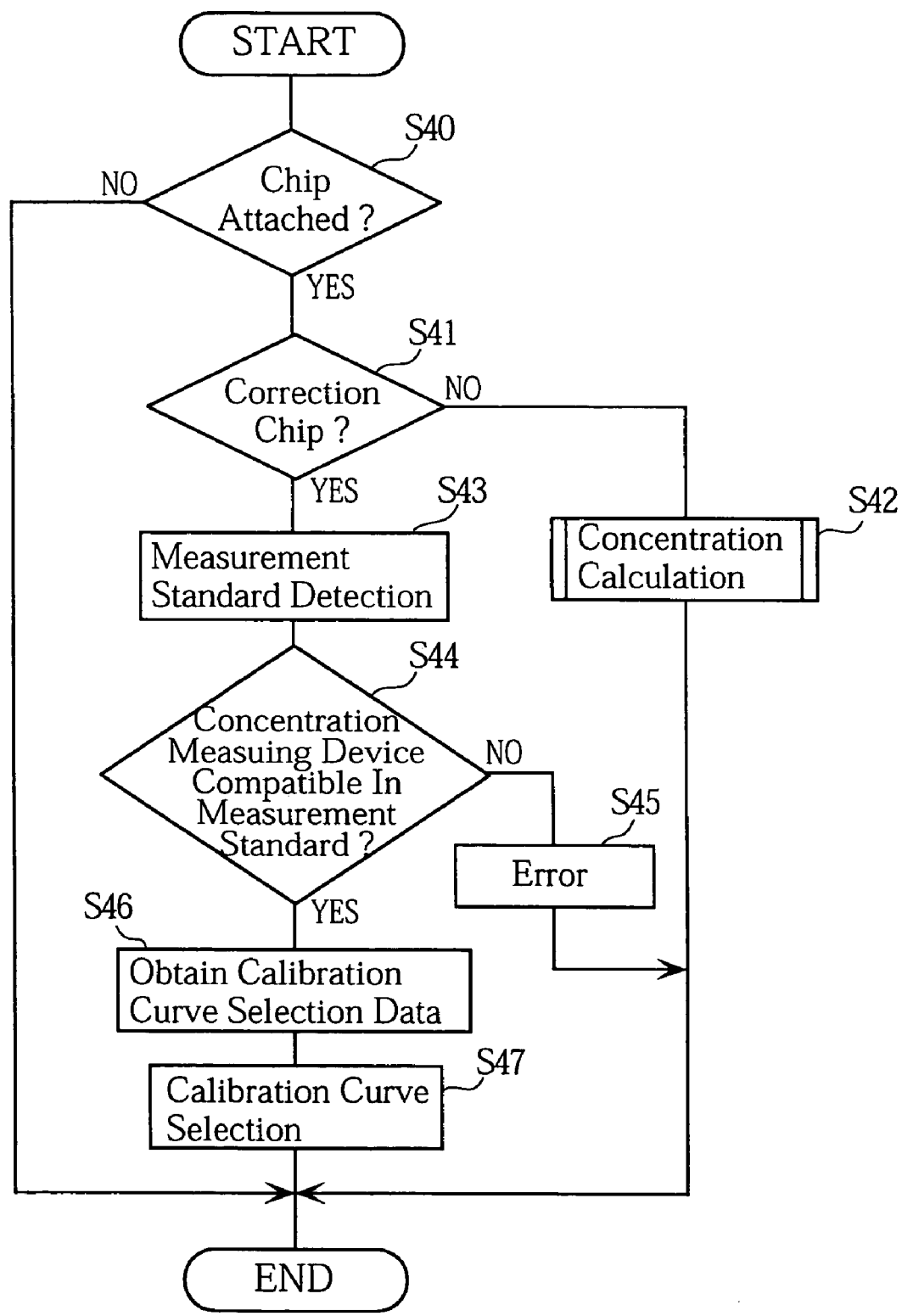
FIG. 23 is a flowchart illustrating the concentration measuring operation of the concentration measuring device according to the eighth embodiment of the present invention.

Next, the operation of the concentration measuring device 1B is described with reference to the flowchart of FIG. 23.

The detection unit 15 of the concentration measuring device 1B detects whether or not the correction chip 5 or the biosensor 3J (these elements are collectively referred to as "attachment" below) is mounted (S40). The determination may be performed by detecting whether or not a current flows when a voltage is applied across the first and fifth terminals 40a, 40e.

When the detection unit 15 detects that the attachment 5, 3J is attached to the concentration measuring device 1B (S40: YES), the unit determines that the attachment is either of the correction chip 5 and the biosensor 3J (S41). This decision of the detection unit 15 may be made based on the current flowing at the second and third terminals 40b, 40c or at the third and fourth terminals 40c, 40d. If the detection unit 15 determines that the attachment is the biosensor 3J (S41:NO), concentration measuring calculation is performed (S42). The calculation is performed by the same steps as described above with reference to FIG. 9.

On the other hand, if the detection unit 15 determines that the attachment is the correction chip 5 (S41:YES), the measurement standard of the biosensor 3J is recognized (S43). The recognition of the measurement standard applied to the biosensor 3J can be performed by obtaining a combination of open-short signals between the second and third terminals 41b, 41c and between the third and fourth terminals 41c, 41d.

Next, it is determined whether or not the measurement standard of the biosensor 3J is compatible with that of the concentration measurement device 1B (S44). This determination is performed in the judging unit 17, for example.

If the judging unit 17 determines that the measurement standard of the biosensor 3J is not compatible with that of the concentration measurement device 1B (S44:NO), an error handling is performed (S45). In the error handling, the user is informed via a sound or by a visual message that the measurement cannot be performed by the biosensor 3J. It is possible that the concentration measuring device 1B may be designed to cope with a plurality of measurement standards and to select the most suitable standard for that of the biosensor 3J based on the measurement standard information from the correction chip.

When the judging unit 17 determines that the measurement standard of the biosensor 3J matches the measurement standard of the concentration measuring device 1B (S44:YES), the detection unit 15 obtains calibration curve selection information from the correction chip 5 (S46). The calibration curve selection information is obtained as a current when a constant voltage is applied to the chip resistor 54. The current correlates with the resistance of the chip resistor 54. Therefore, the correction chip 5 can be designed to output the desired calibration curve selection information depending on the resistance selected for the chip resistor 54, while the concentration measuring device 1B obtains the calibration curve selection information suitable for the sensitivity of the biosensor 3J.

Next, the concentration measuring device 1B selects the most suitable calibration curve for the biosensor 3J from the calibration curves stored in the storage unit 14. Once the selection of the calibration curve is performed, the concentration calculation is performed based on the selected calibration curve until another calibration curve is selected by the attaching of a correction chip 5.

Further, the concentration measuring operation is terminated when the detection unit 15 determines that the attachment 3J, 5 is not mounted (S40:NO), when the concentration measurement (S42) is terminated, or when the error handling is terminated (S45).

In this embodiment, it is determined whether or not the measurement standard of the biosensor 3J is compatible with the measurement standards adopted for the concentration measuring device 1B. When necessary, the error handling is performed. With this arrangement, it is possible to avoid an incorrect concentration measurement which would result from the discrepancy between the measurement standard of the biosensor and the measurement standard of the concentration measuring device 1B. Further, when the concentration measuring device 1B is designed to cope with a plurality of measurement standards, the device can select the measurement standard most suitable for the biosensor 3J set to the correction chip 5 to calculate the concentration based on the standard.

The measurement standard information output section 53 of the correction chip 5 may have the same structure as the attribute information output section of the described biosensor 2, 3A-3I (see FIG. 2, 10, 11-18).

Figure 24:
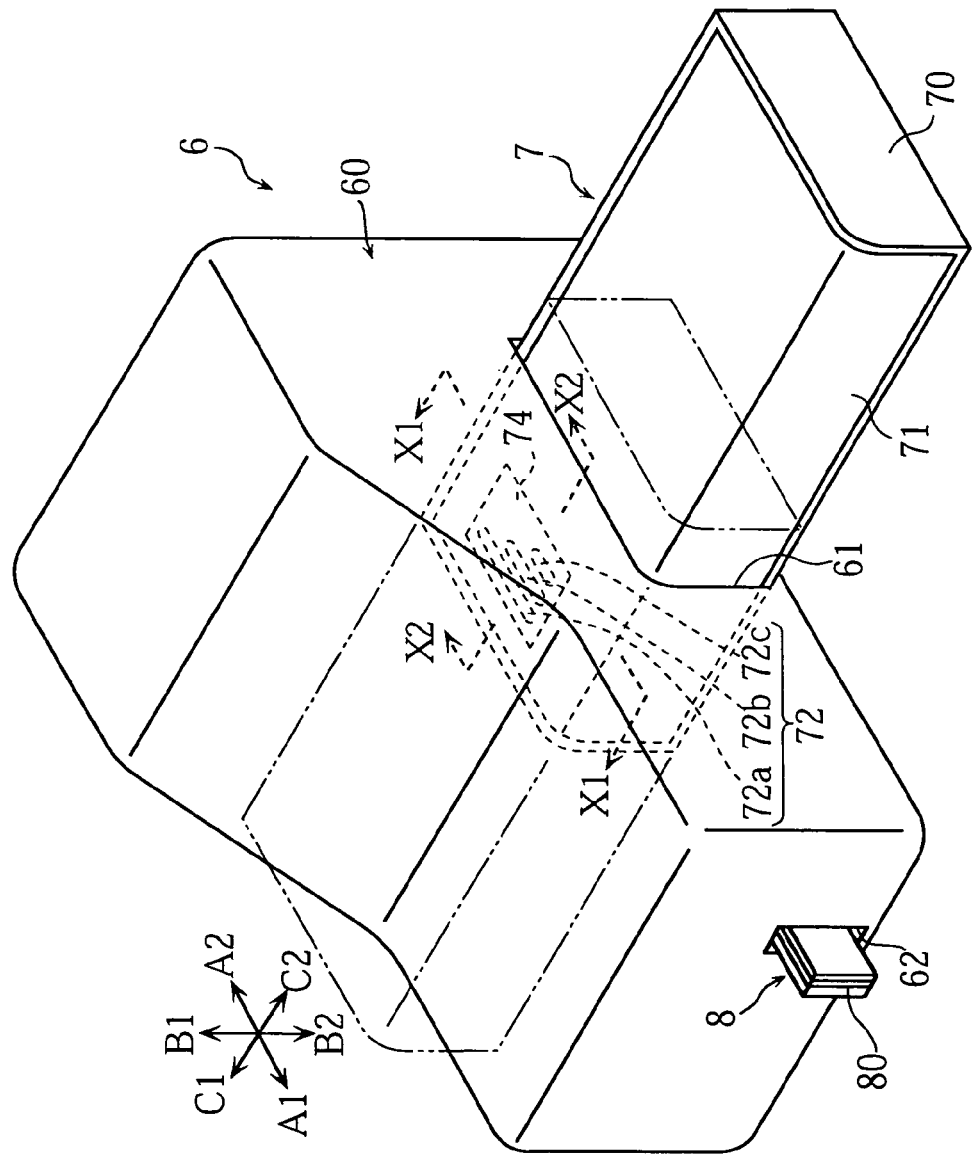
FIG. 24 is a perspective view showing a concentration measuring device with a sensor cartridge according to a ninth embodiment of the present invention.
Figure 25:
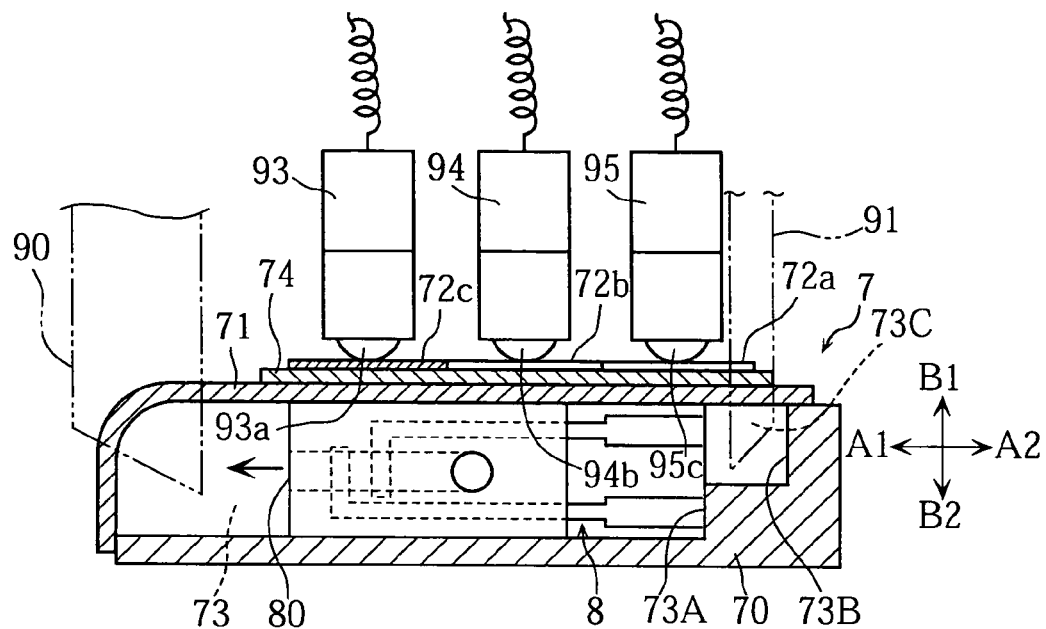
FIG. 25 is a sectional view taken along lines X1-X1 of FIG. 24, extracting a principal portion.
Figure 26:
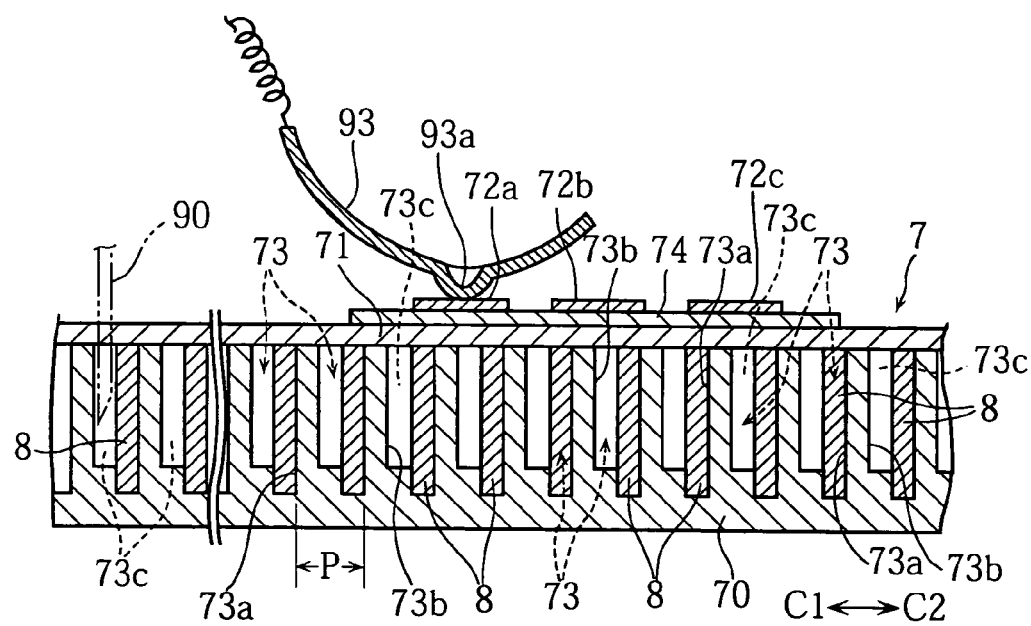
FIG. 26 is a sectional view taken along lines X2-X2 of FIG. 24, extracting a principal portion.

FIGS. 24 through 27 show a ninth embodiment of the present invention. FIG. 24 is a perspective view showing the concentration measuring device with a sensor cartridge. FIGS. 25 and 26 are sectional views taken along lines X1-X1 and X2-X2. FIG. 27 is an enlarged view showing a principal portion of the sensor cartridge.

As shown in FIG. 24, a concentration measuring device 6 is used with a sensor cartridge 7. As shown in FIGS. 25 and 26, the sensor cartridge 7 accommodates a plurality of biosensors 8. The concentration measuring device 6 takes one of the biosensors 8 out of the sensor cartridge 7 to measure a concentration of a specific component in a sample liquid with the biosensor 8.

The concentration measuring device 6 has a housing 60 (see FIG. 24) internally provided with a push mechanism for pushing the biosensor 8 in the direction of an arrow A1 in FIG. 24, a transfer mechanism for transferring the biosensor 8, and an index mechanism for sequentially shifting the sensor cartridge 7 bit by bit. The transfer mechanism and the index mechanism may be known means. Similarly to the concentration measuring device 1 shown in FIG. 1, the concentration measuring device 6 includes a voltage applying unit, an electric current measuring unit, a storage unit, a calibration curve selection unit, a judging unit, a detection unit, a control unit, and a calculating unit.

As shown in FIG. 24, the housing 60 is formed with a cartridge mount 61 and an opening 62. The cartridge mount 61 allows the movement of sensor cartridge 7, holds the sensor cartridge 7 and guides the sensor cartridge 7 being indexed. The opening 62 communicates with the cartridge mount 61 so as to allow the biosensor 8 to project to the outside after is transferred by the transfer mechanism.

The sensor cartridge 7 includes a case 70, a sealing film 71, and an attribute information output section 72.

As shown in FIGS. 25 and 26, the case 70 includes a plurality of sensor holders 73. The sensor holder 73 is open forward (in the direction of an arrow A1 shown in FIGS. 24 and 25) and upward (in the direction of an arrow B1 shown in FIGS. 24 and 25). As clearly shown in FIG. 26, the sensor holders 73 are disposed at a pitch P in the longitudinal direction (in directions of arrows C1, C2), where the pitch P corresponds to the indexing pitch of the index mechanism for the sensor cartridge 7. Each sensor holder 73 accommodates one sensor 8. As understood from FIG. 25, the biosensor 8 has a structure where the attribute information output section and the correction information output section are omitted from the biosensor shown in FIG. 2. As clearly shown in FIGS. 25 and 26, the biosensor 8 is accommodated in the sensor holder 73 in a manner such that the sample liquid inlet 80 faces in the transferring direction A1 of the biosensor, and that the sensor is held in direct contact with a side surface 73a and an upright step portion 73A. In this state, the biosensor 8 is spaced from side surfaces 73b and 73B with gaps 73c, 73C.

As shown in FIGS. 24 and 26, the sealing film 71 is applied to cover the sensor holders 73 collectively. The sealing film 71 may be made of metal thin film or plastic film, or formed by combining these films.

FIG. 25 shows a draw-out mechanism including first and second cutters 90, 91 depicted in imaginary lines. The draw-out mechanism includes first and second cutters 90, 91. The first cutter 90 is movable upward and downward or in the directions B1, B2. Moving downward, the first cutter 90 makes a cut in the sealing film 71 at the front portion relative to the biosensor 8. At this time, the first cutter 90 plunges into the gap 73c as shown in FIG. 26. The second cutter 91 shown in FIG. 25 is movable upward and downward or in the directions B1, B2, and forward and backward or in the direction A1, A2. Moving downward, the second cutter 91 makes a cut in the rear portion of the sealing film 71. At this time, the second cutter 91 plunges into the gap 73c.

After the sealing film 71 is cut by the first and second cutters 90, 91, the first cutter 90 is moved upward B1 and the second cutter 91 is moved forward A1, thereby moving the biosensor 8 out of the sensor cartridge 7. The biosensor 8 is further moved forward A1 by the transfer mechanism. The biosensor 8 with the sample liquid inlet 80 is partly projected from the opening 62 of the housing 60.

As shown in FIGS. 24 and 27, the attribute information output section 72, formed on a sheet 74, has a plurality of individual information output sections 72a, 72b, 72c. The sheet 74 is adhered on to the sealing film 71. The individual information output sections 72a-72c are strips formed by e.g. screen printing and extending widthwise of the sensor cartridge 7. The attribute information output section 72 may consist of one conductor.

As shown in FIGS. 25 and 26, the concentration measuring device 6 has a calibration curve selection unit (not shown) selecting the calibration curve based on calibration curve determination information detected via first-third terminals 93-95. The terminals 93-95 are located so as to contact the individual information output sections 72a-72c in inserting the sensor cartridge 7. The terminals 93-95 are leaf springs to press the sensor cartridge 7 downward. The terminals 93-95 is provided with pivots 93a, 94b, 95c, respectively. The pivots 93a-95c provide point-contacts between the terminals 93-95 and the individual information output sections 72a-72c, respectively.

When the individual information output sections 72a, 72b, 72c contact the terminals 93-95 respectively, a constant voltage is applied to the output sections. Then, the individual information output sections 72a, 72b, 72c output the specific information as a current or an open-short signal. The attribute information is obtained as a set of several kinds of specific information. The calibration curve selection unit (not shown) determines the calibration curve suitable for the sensitivity of the biosensor 8 based on the calibration curve selection information. The judging unit (not shown) judges whether or not the measurement standard of the biosensor 8 matches that of the concentration measuring device 6 (see FIG. 1).

In the concentration measurement, the biosensor 8 projecting from the housing 60 is introduced with a sample liquid via the sample liquid inlet 80. According to the sequence shown in FIG. 9, the concentration measuring device 6 calculates the concentration of the specific components in the sample liquid (see FIG. 1).

In this embodiment, just attaching the sensor cartridge 7 to the concentration measuring device 6 enables the determination of the calibration curve suitable for the sensitivity of the biosensor 8 in the sensor cartridge 7, while judging whether or not the measurement standard of the biosensor 8 matches that of the concentration measuring device 6. Therefore, the calibration curve determination can be performed without attaching the correction chip or button operation. The user has no role in the determination of the calibration curve, which results in preventing failure of the calibration curve determination due to user's carelessness.

The invention claimed is:

1. A measurement instrument which is attached to a concentration measuring device for calculating a concentration based on concentration calculation information and is capable of outputting the concentration calculation information to the concentration measuring device, the measurement instrument comprising,
a working electrode,
a counterpart electrode paired with the working electrode,
a reagent part bridging between the working electrode and the counterpart electrode, and
an attribute information output section for outputting attribute information relating to an attribute of the measurement instrument as an electric physical quantity,
wherein the attribute information output section comprises a plurality of attribute-indicating electrodes provided in addition to the working electrode and the counterpart electrode, and a plurality of connection-breakable parts bridging between the attribute-indicating electrodes, and
wherein the attribute information correlates with a resistance of the attribute information output section.

2. The measurement instrument according to claim 1, wherein the attribute information is utilized for enabling the concentration measuring device to select a calibration curve suitable for the measurement instrument.

3. The measurement instrument according to claim 2, wherein the attribute information is utilized for enabling the concentration measuring device to select a calibration curve suitable for sensitivity of the measurement instrument.

4. The measurement instrument according to claim 1, wherein the attribute information relates to a measurement standard applied to the measurement instrument.

5. The measurement instrument according to claim 1, further comprising a substrate at least having an end portion inserted into the concentration measuring device for concentration measurement.

6. The measurement instrument according to claim 1, further comprising: a substrate having an end portion inserted into the concentration measuring device for concentration measurement;
wherein the attribute-indicating electrodes of the attribute information output section are provided between the working electrode and the counterpart electrode.

7. The measurement instrument according to claim 1, wherein the attribute-indicating electrodes of the attribute information output section are brought into contact with terminals of the concentration measuring device, and
wherein the attribute information is provided in the attribute information output section by selectively breaking or leaving intact at least one of the connection-breakable parts.

8. The measurement instrument according to claim 1, further comprising a correction information output section for outputting correction information correlating with a discrepancy between an actual resistance of the attribute information output section and a resistance preset for the attribute information output section.

9. The measurement instrument according to claim 1, wherein the attribute information output section is arranged to output identification information for informing the concentration measuring device that the measurement instrument is arranged to output the concentration calculation information.

10. A method of making a measurement instrument as defined in claim 1, the method comprising disconnecting at least one of the connection-breakable parts in accordance with information outputted from the attribute information output section.

11. The measurement instrument according to claim 1, wherein the attribute information output section also outputs measurement standard information regarding a measurement standard applied to the measurement instrument.

12. A combination of a concentration measuring device and the measurement instrument defined in claim 1 for attachment to the concentration measuring device, the concentration measuring device comprising:
a recognizer for detecting the attribute information from the measurement instrument,
wherein a concentration calculation-related operation is performed based on the attribution information detected by the recognizer.

13. The combination of the concentration measuring device and the measurement device according to claim 12, wherein the attribute information output section is arranged to output calibration curve selection information, as the attribution information, for selecting a calibration curve suitable for the measurement instrument, the concentration measuring device further comprising: a storage unit storing information regarding a plurality of calibration curves; and a calibration curve selection unit selecting a specific calibration curve suitable for the measurement instrument from the plurality of calibration curves.

14. The combination of the concentration measuring device and the measurement device according to claim 12, wherein the attribute information output section is arranged to output measurement standard information, as the attribution information, regarding a measurement standard applied to the measurement instrument, the concentration measuring device further comprising a judging unit determining whether it is possible or not to perform concentration measurement with the measurement instrument based on the attribute information.

15. The combination of the concentration measuring device and the measurement device according to claim 12, wherein the recognizer comprises a plurality of terminals brought into contact with the attribute-indicating electrodes of the attribute information output section, the recognizer being arranged to detect the attribute information when constant voltage or constant current is applied to the attribute information output section via the terminals.

16. A measurement instrument which is attached to a concentration measuring device for calculating a concentration based on concentration calculation information and is capable of outputting the concentration calculation information to the concentration measuring device, the measurement instrument comprising,
  a working electrode,
  a counterpart electrode paired with the working electrode,
  a reagent part bridging between the working electrode and the counterpart electrode, and
  an attribute information output section for outputting attribute information relating to an attribute of the measurement instrument as an electric physical quantity,
  wherein the attribute information output section comprises a plurality of attribute-indicating electrodes provided in addition to the working electrode and the counterpart electrode, and a plurality of connection-breakable parts bridging between the attribute-indicating electrodes, and
  wherein the attribute information output section is arranged to output identification information for informing the concentration measuring device that the measurement instrument is arranged to output the concentration calculation information.

* * * * *